United States Patent [19]

Gelfand et al.

[11] Patent Number: 5,418,149
[45] Date of Patent: May 23, 1995

[54] REDUCTION OF NON-SPECIFIC AMPLIFICATION GLYCOSYLASE USING DUTP AND DNA URACIL

[75] Inventors: David H. Gelfand, Oakland; Shirley Y. Kwok, San Ramon; John J. Sninsky, El Sobrante, all of Calif.

[73] Assignee: Hoffmann-La Roche Inc., Nutley, N.J.

[21] Appl. No.: 960,362
[22] PCT Filed: Jul. 23, 1991
[86] PCT No.: PCT/US91/05210
 § 371 Date: Jan. 5, 1993
 § 102(e) Date: Jan. 5, 1993
[87] PCT Pub. No.: WO92/01814
 PCT Pub. Date: Feb. 6, 1992

Related U.S. Application Data

[63] Continuation-in-part of Ser. No. 557,517, Jul. 24, 1990, abandoned, which is a continuation-in-part of Ser. No. 609,157, Nov. 2, 1990, abandoned.

[51] Int. Cl.⁶ .......................... C12Q 1/68; C12P 19/34
[52] U.S. Cl. .......................... 435/91.2; 435/6
[58] Field of Search ........................... 435/91.2, 6

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,873,192 | 10/1989 | Kunkel | 435/172.3 |
| 4,965,188 | 10/1990 | Mullis | 436/6 |
| 5,035,996 | 7/1991 | Hartley | 435/6 |

FOREIGN PATENT DOCUMENTS

| | | |
|---|---|---|
| 0329822 | 8/1989 | European Pat. Off. |
| 0415755 | 3/1991 | European Pat. Off. |
| 0401037 | 12/1991 | European Pat. Off. |
| 8706270 | 10/1987 | WIPO |
| 8911548 | 11/1989 | WIPO |
| 9006995 | 6/1990 | WIPO |

OTHER PUBLICATIONS

Chu et al., 1986, Nuc. Acids Res. 14(14):5591–5603, "Synthesis of an Amplifiable Reporter RNA for Bioassays".

Lizardi et al., 1988, Biotechnology 6:1197–1202, "Exponential Amplification of Recombinant-RNA Hybridization Probes".

Wu and Wallace, 1989, Genomics 4:560–569, "The Ligation Amplification Reaction (LAR)-Amplification of Specific DNA Sequences Using Sequential Rounds of Template-Dependent Ligation".

Landegren et al., 1988, Science 241:1077–1080, "A Ligase-Mediated Gene Detection Technique".

Sancar and Sancar, 1988, Ann. Rev. Biiochem. 57:29–67, "DNA Repair Enzymes".

Lindahl, 1982, Ann. Rev. Biochem. 51:61–87, "DNA Repair Enzymes".

Kane and Linn, 1981, J. Biological Chemistry 256(7):3405–3414, "Purification and Characterization of an Apurinic/Apyrimidinic Endonuclease from HeLa Cells".

Verly et al., 1981, Eur. J. Biochem. 118:195–201, "Localization of the Phosphoester Bond Hydrolyzed... the Major Apurinic/Apyrimidinic Endodeoxyribonuclease from Rat-Liver Chromatin".

Shaper et al., 1982, J. Biological Chemistry 257(22):13455–13458, "Human Placental Apurinic-/Apyrimidinic Endonuclease".

(List continued on next page.)

Primary Examiner—Margaret Parr
Assistant Examiner—David Schreiber
Attorney, Agent, or Firm—George M. Gould; Stacey R. Sias; Douglas A. Petry

[57] ABSTRACT

Improved methods for amplifying nucleic acids can reduce non-specific amplification and minimize the effects of contamination of nucleic acid amplification reaction assays due to amplified product from previous amplifications. The methods involve the introduction of unconventional nucleotide bags into the amplification reaction products and treating the products by enzymatic (e.g., glycosylases) and/or physical-chemical means to render the product incapable of acting as a template for subsequent amplifications.

4 Claims, No Drawings

OTHER PUBLICATIONS

Nakabeppu et al., 1984, J. Biological Chemistry 259(22):13723–13729, "Cloning and Characterization of the alkA Gene of Escherichia coli that Encodes 3-Methyladenine DNA Glycosylase II".

Steinum and Seeberg, 1986, Nuc. Acids Res. 14(9):3763–3773, "Nucleotide Sequence of the tag Gene from Escherichia coli".

Radman, 1976, J. Biological Chemistry 251(5):1438–1445, "An Endonuclease from Escherichia coli That Introduces Single Polynucleotide Chain Scissions in Ultraviolet-Irradiated DNA".

Gates III and Linn, 1977, J. Biological Chemistry 252(5):1647–1653, "Endonuclease V of Escherichia coli".

Gates III and Linn, 1977, J. Biological Chemistry 252(9):2802–2807, "Endonuclease from Escherichia coli That Acts Specifically Upon Duplex DNA Damaged by Ultraviolet LIght, Osmium Tetroxide, Acid, or X-rays".

Demple et al., 1980, Methods of Enzymology 65:224–231, "Purification of Properties of Escherichia coli Endodeoxyibonuclease V".

Varshney et al., 1988, J. Biological Chemistry 263(16:7776–7784, "Sequence Analysis, Expression, and Conservation of Escherichia coli Uracil DNA Glycosylase and Its Gene (ung)".

Morgan and Chlebek, 1989, J. Biological Chemistry 264(17):9911–9914, "Uracil-DNA Glycosylase in Insects".

Duncan et al., 1978, J. Bacteriology 134(3):1039–1045, "Escherichia coli K-12 Mutants Deficient in Uracil-DNA Glycosylase".

Kunkel, 1985, Proc. Natl. Acad. Sci. USA 82:488–492, "Rapid and Efficient Site-Specific Mutagenesis Without Phenotypic Selection".

Bio-Rad Muta-Gene in vitro Mutagenesis Kit Instruction manual, Jul., 1987.

Warner and Duncan, 1978, Nature 272:32–34, "In Vivo Synthesis and Properties of Uracil-Containing DNA".

Warner et al., 1979, J. Biological Chemistry 254(16):7534–7539, "The Properties of a Bacteriophage T5 Mutant Unable to Induce Deoxyuridine 5'-Triphosphate Nucleotidohydrolase".

Sagher and Strauss, 1983, Biochemistry 22:4518–4526, "Insertion of Nucleotides Opposite Apurinic/Apyrimidinic Sites in Deoxyribonucleic Acid During In Vitro Synthesis: Uniqueness of Adenine Nucleotides".

Sagher and Strauss, 1985, Nuc. Acids. Res. 13(12):4285–4298, "Abasic Sites From Cytosine as Termination Signals for DNA Synthesis".

Sedwick et al., 1986, Mutation Research 162(1):7–20, "Deoxyuridine Miscorporation Causes Site-Specific Mutational Lesions in the lacI Gene of Escherichia coli".

Kwok, 1990, PCR Protocols (ed. Innis et al., Academic Press), Chaper 17, pp. 142–145, "Procedures to Minimize PCR-Product Carry-Over".

Sarkar and Sommer, 1990, nature 343:27, "Shedding Light on PCR Contamination".

Kitchin et al., 1990, Nature 344:201, "Avoidance of False Positives".

Diagnostics Report of Sep., 1988.

Longo et al., 1990, Gene 93:125–128, "Use of Uracil DNA Glycosylase to Control Carry-Over Contamination in Polymerase Chain Reactions".

Guatelli et al., 1990, Proc. Natl. Acad. Sci. USA 87:1874–1878, "Isothermal, in vitro Amplification of Nucleic Acids by a Multienzyme Reaction Modeled After Retroviral Replication".

Kwoh et al., 1989, Proc. Natl. Acad. Sci. USA 86:1173–1177, "Transcription-Based Amplification System and Detection of Amplified Human Immunodeficiency Virus Type 1 With a Bead-Based Sandwich Hybridization Format".

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
( A ) LENGTH: 28 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 1:

ACCCATGTAC CCTACAATCC CACCAGCT                                28

( 2 ) INFORMATION FOR SEQ ID NO: 2:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 2:

GTGGTGGATT TGCCATCGGG TTTT                                    24

( 2 ) INFORMATION FOR SEQ ID NO: 3:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 3:

AGTGGGGGGA CATCAAGCAG CCATGCAAAT                              30

( 2 ) INFORMATION FOR SEQ ID NO: 4:

( i ) SEQUENCE CHARACTERISTICS:
( A ) LENGTH: 27 bases ( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 4:

TGCTATGTCA GTTCCCCTTG GTTCTCT         27

( 2 ) INFORMATION FOR SEQ ID NO: 5:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 5:

AGTTGGAGGA CATCAAGCAG CCATGCAAAU         30

( 2 ) INFORMATION FOR SEQ ID NO: 6:

( i ) SEQUENCE CHARACTERISTICS:
( A ) LENGTH: 27 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 6:

TGCTATGTCA GTTCCCCTTG GTTCTCU         27

( 2 ) INFORMATION FOR SEQ ID NO: 7:

( i ) SEQUENCE CHARACTERISTICS:
( A ) LENGTH: 29 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 7:

AGTTGGAGGA CATCAAGCAG CCATGCAAT         29

( 2 ) INFORMATION FOR SEQ ID NO: 8:

( i ) SEQUENCE CHARACTERISTICS:
( A ) LENGTH: 33 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 8:

GAGACCATCA ATGAGGAAGC TGCAGAATGG GAT         33

( 2 ) INFORMATION FOR SEQ ID NO: 9:

( i ) SEQUENCE CHARACTERISTICS:
( A ) LENGTH: 28 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 9:

CCGCATATGG CTAACGAATT AACCTGGC                                             28

( 2 ) INFORMATION FOR SEQ ID NO: 10:

( i ) SEQUENCE CHARACTERISTICS:
( A ) LENGTH: 31 bases
( B ) TYPE: nucleic acid
( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 10:

CGAGATCTCA CTCACTCTCT GCCGGTAATA C                                         31

REDUCTION OF NON-SPECIFIC AMPLIFICATION GLYCOSYLASE USING DUTP AND DNA URACIL

CROSS-REFERENCE TO RELATED APPLICATIONS

The present application is the National Phase of PCT/US91/05210, filed Jul. 23, 1991, which is a continuation-in-part (CIP) application of U.S. Ser. No. 07/609,157, filed Nov. 24, 1990, now abandoned, which is a CIP application of U.S. Ser. No. 07/557,517, filed Jul. 24, 1990, now abandoned.

FIELD OF THE INVENTION

This invention relates to improved methods for amplifying nucleic acids using methods such as the polymerase chain reaction (PCR) procedure. More specifically this invention provides methods to increase the specificity of nucleic acid amplification assays and to minimize the effects of aerosol contamination of nucleic acid amplification reaction assays due to amplified product from previous amplifications. The methods involve the introduction of unconventional nucleotide bases into the amplified product and exposing carryover product to enzymatic (e.g., glycosylases) and/or physical-chemical treatment that effectively render the product incapable of acting as a template for subsequent amplifications,. This invention also relates to methods for producing nucleic acid-free proteins that are particularly useful as reagents for amplification systems. This invention further relates to efficient means to express uracil-DNA glycosylase and purified preparations of uracil-DNA glycosylase.

DESCRIPTION OF THE PRIOR ART

The incorporation of deoxyuridine into the genome of *E. coil* has been reported to be especially high in strains having a defective deoxyuridine-triphosphatase. See Sedwick et al., 1986, *Mutat. Res.* 162(1):7–20. DNA with abasic sites has been prepared by deamidation of cytosine followed by treatment with uracil-DNA glycoslyase. DNA polymerase extension on these templates is terminated by abasic sites. See Sagher and Strauss, 1983, *Nucleic Aids Res.* 13(12):4285–4298 and Sagher and Strauss, 1983, *Biochemistry* 22(19):4518–4526. DNA repair enzymes have been reviewed by Sancar and Sancar, 1988, *Ann. Rev. Biochem.* 57:29–67, and Lindahl, 1982, *Ann. Rev. Biochem.* 51:61–87.

A method for introducing site-specific mutations into DNA has been described that relies upon replacement of thymine with uracil in DNA and subsequent treatment with uracil-DNA glycosylase. See U.S. Pat. No. 4,873,192 and Kunkel, 1985, *Proc. Natl. Acad. Sci. USA* 82:488–492. Uracil-containing phage were suggested as a part of a biological containment system that would transfer generic information only to uracil-N glycosylase deficient cells and not to naturally occurring bacteria. See Warner et al., 1979, *J. Biol. Chem.* 245(16):7534–7539.

Contamination from Carryover products is a recognized problem. See Kwok, *PCR Protocols* (Innis et al. Academic Press 1990), Chapter 17, pages 142–145.

SUMMARY OF THE INVENTION

The present invention provides methods to increase the specificity of nucleic acid amplification processes. The method involves the incorporation of modified nucleotides and a nucleic acid glycosylase specific for the modified nucleotides into the amplification reaction mixture so that non-specific amplification products generated prior to deactivation of the glycosylase are degraded by the glycosylase and rendered incapable of serving as templates for amplification. In amplification processes involving a heat denaturation step to denature double-stranded nucleic acids into single-stranded nucleic acids, the increased specificity provided by the present methods results from degradation of non-specific amplification products generated prior to the first denaturation step.

This invention also provides for methods of "sterilizing" or "restricting" nucleic acid amplification reaction systems contaminated with nucleic acids generated from previous amplifications. The method of the invention involves the generation of nucleic acids that can be rendered incapable of further amplification, so that if amplified nucleic acids produced by the method contaminate an amplification mixture, that contaminated mixture can be treated so that the contaminating nucleic acids are not amplified.

These sterilizing methods comprise: (a) mixing conventional and unconventional nucleotides into an amplification reaction system containing an amplification reaction mixture and a target nucleic acid sequence; (b) amplifying the target nucleic acid sequence to produce amplified products of nucleic acid having the unconventional nucleotides and conventional nucleotides incorporated therein; and (c) degrading any amplified product that contaminates a subsequent amplification mixture by hydrolyzing covalent bonds of the unconventional nucleotides. The contaminating product is also called "carryover" product.

Carryover typically occurs from aerosol or other means of physically transferring amplified product generated from earlier amplification reactions into a different, later, amplification reaction. Carryover contamination may also result from traces of nucleic acid which originate with the amplification reagents.

In particular, the degradation of an amplified product or carryover contaminant is accomplished by treating the nucleic acid with a DNA glycosylase specific for the unconventional nucleotide. The preferred unconventional bases are alkylated bases such as N-7 methylguanine, 3-methyladenosine, uracil, and hypoxanthine. Preferred glycoslyases include those selected from the group consisting of uracil-DNA glycosylase, hypoxanthine-DNA glycosylase, 3-methyladenine-DNA glycosylase I, and 3-methyladenine-DNA glycosylase II. Once the glycosylase has removed bases from the nucleic acid, the nucleic acid chain can be cleaved at the abasic sites by treatment with an alkaline reagent, an AP endonuclease, hat, or by a combination of such treatment steps.

The amplification systems to which the methods of this invention apply include the polymerase chain reaction system (U.S. Pat. Nos. 4,683,195; 4,683,202; and 4,965,188), the ligase amplification system (PCT Patent Publication No. 89/09835), the self-sustained sequence replication system (EP No. 329,822 and PCF Patent Publication No. 90/06995), the transcription-based amplification system (PCT Patent Publication No. 89/01050 and EP No. 310,229), and the Qβ RNA replicase system (U.S. Pat. No. 4,957,858). Each of the foregoing patents and publications is incorporated herein by reference.

In one embodiment, the sterilizing method encompasses degrading any contaminating amplified product with uracil-DNA glycosylase in an aqueous solution containing a target nucleic acid sequence; inactivating the glycosylase (such as by heat denaturation); and, amplifying the target sequence. The degradation of the contaminating amplified product may be accomplished while the product is in contact with a nucleic acid amplification reaction system. Thus, one can prepare a sample for amplification, treat the sample by the present method to degrade any contaminating nucleic acid generated by a previous amplification, and then amplify the target nucleic acid in the sample without having to adjust reaction volume or composition between steps.

In particular, the sterilizing method of the invention prevents nucleic acids generated from an amplification system from serving as templates in a subsequent amplification system, and comprises: (a) mixing 2'-deoxyuridine 5'-triphosphate into a reaction compartment containing a PCR amplification mixture and a target nucleic acid sequence; (b) amplifying the target nucleic acid sequence to produce amplified products of DNA having the deoxyuridine incorporated therein; and (c) degrading any amplified product that contaminates a subsequent amplification reaction with uracil-DNA glycosylase.

Uracil-DNA glycosylase, also known as uracil N-glycosylase or UNG, has significant ability to regain activity following heat denaturation. Because LING activity is not desirable in the amplification reaction mixture after the initial treatment to improve specificity or to remove contaminating nucleic acids, the present invention also provides thermolabile UNG derivatives, and methods for generating and using such derivatives, that do not regain activity after heat denaturation. In a broader aspect, the invention encompasses a restriction/sterilization method in which any irreversibly thermolabile glycosylase is used to render abasic unconventional nucleotides incorporated into a nucleic acid strand.

This invention further provides for an amplification tube containing the amplification reagents together with the sterilization or improved specificity providing reagents of the present invention. For PCR, the tube will contain conventional nucleoside triphosphates, unconventional nucleoside triphosphates, a polymerase, preferably a thermostable polymerase, and a glycosylase specific for the modified nucleotides. In particular, the tube may contain 2'-deoxyuridine 5'-triphosphate and uracil-DNA glycosylase together with PCR reagents. Depending on the purpose for which the amplified DNA is generated, the PCR reagents might not contain dTYP. For other amplification systems, the reaction robe will contain the reagents more fully described below.

This invention further provides for a kit comprising a multiplicity of compartments, the compartments containing amplification reagents and the sterilization or improved specificity providing reagents of the present invention. For PCR, the kit can contain conventional nucleoside triphosphates, unconventional nucleoside triphosphates, a thermostable or other polymerase, and nucleoside glycosylase specific for the unconventional nucleoside.

In particular, a PCR kit may contain deoxyuridine 5'-triphosphate and uracil-DNA glycosylase and/or a thermostable polymerase derived from *Thermus aquaticus*. A thermostable polymerase "derived" from *T. aquaticus* would include polymerase purified from native sources, e.g., *T. aquaticus*, and from cells altered by recombinant genetics to express such polymerases or analogs thereof. In a preferred embodiment, the kit comprises only uracil N-glycosylase and dUTP. The uracil N-glycosylase is preferably at a concentration of about 0.2 to 2 units/$\mu$l and is supplied in a 0.5 ml microfuge tube filled to about 100 to 200 $\mu$gl. The dUTP is preferably at a concentration of 10 to 30 mM and is supplied in a 0.5 or 1.5 ml microfuge tube filled to about 300 to 500 $\mu$l.

This invention also provides improved methods for purifying a recombinant or native protein from a host cell. The improvement relates to the elimination of contaminating nucleic acid. For recombinant proteins, these methods comprise: (a) transforming a host cell with a vector capable of directing the expression of the recombinant protein, said host cell being deficient in a specific nucleoside N-glycosylase recognizing a specific unconventional nucleotide; (b) culturing the cell under conditions permitting the expression of the recombinant protein and the stable incorporation of the specific unconventional nucleoside into the host cell nucleic acid; (c) isolating the recombinant protein from host cells; and (d) contacting the isolated protein with nucleoside glycosylase able to recognize the specific unconventional nucleotide under conditions that permit the glycosylase to degrade nucleic acids comprising the specific unconventional nucleotides.

Preferred specific unconventional nucleosides for this purification process are deoxyribouracil (deoxyuridine), inosine, and. N-7 methylguanosine. In one embodiment, the host cell is a prokaryote, preferably deficient for uracil-DNA glycosylase or both uracil-DNA glycosylase (UNG-) and deoxyuridine triphosphatase (dut-). The method has particular advantages for the expression and purification of proteins used in amplification systems; such proteins include DNA polymerase (e.g., Taq DNA polymerase), DNA ligase, RNA ligase, reverse transcriptase, RNA replicase, RNA polymerase, RNAse, or RNAsin.

In particular, this method for producing a recombinant protein comprises: (a) transforming a host cell with a vector capable of directing the expression of the protein, said host being deficient for a specific unconventional nucleoside glycosylase recognizing a specific unconventional nucleotide; (b) culturing the cell under conditions permitting the expression of the protein and the stable incorporation of the specific unconventional nucleoside into the host cell nucleic acid; (c) isolating the protein from the host cells; and (d) contacting the isolated protein with nucleoside glycosylase able to recognize the specific unconventional nucleotide under conditions that permit the glycosylase to degrade nucleic acids comprising the specific unconventional nucleotides. The method is equally applicable to the production of native proteins, except no transformation of the host cell is required.

The present invention also provides processes for purifying uracil N-glycosylase (UNG) from native or recombinant host cells, very pure preparations of UNG, and stabilized, purified preparations of UNG.

DESCRIPTION OF THE PREFERRED EMBODIMENTS

The term "alkaline reagents" refers to reagents or reaction conditions that maintain the pH of a solution containing pH sensitive amplified product to the degree necessary to degrade covalent bonds within the product (e.g., pH 8.0–9.0). The alkaline reagent, in one embodiment, is the amplification reaction buffer.

The term "amplifying" which typically refers to an "exponential" increase in target nucleic acid, is being used herein to describe both linear and exponential increases in the numbers of a select target sequence of nucleic acid.

The term "amplification reaction mixture" refers to an aqueous solution comprising the various reagents used to amplify a target nucleic acid. These include enzymes, aqueous buffers, salts, target nucleic acid, and nucleoside triphosphates. Depending upon the context, the mixture can be either a complete or incomplete amplification reaction mixture.

The term "amplification reaction system" refers to any in vitro means for multiplying the copies of a target sequence of nucleic acid. Such methods include but are not limited to polymerase (PCR), DNA ligase (LCR), Qβ RNA replicase, and RNA transcription-based (TAS and 3SR) amplification systems. These involve multiple amplification reagents and are more fully described below.

The term "amplification reaction tube" refers to a container suitable for holding the amplification reagents. Generally the tube is constructed of inert components so as to not inhibit or interfere with the amplification system being used. Where the system requires thermal cycling or repeated heating and cooling, the tube must be able to withstand the cycling process and fit precisely the wells of the thermocycler.

The term "amplification reagents" refers to the various buffers, enzymes, primers, nucleoside triphosphates, both conventional and unconventional, and probes used to perform the select amplification procedure.

The term "conventional" when referring to nucleic acid bases, nucleosides, or nucleotides refers to those which occur naturally in the polynucleotide being described (i.e., DNA [dA, dG, dC, dT] or RNA [A, G, C, U]).

The term "deficient" refers to the inability of a cell to produce a gene product normally produced by the corresponding "wild type" cell. The deficiency can be either a result of direct genetic mutation of the structural gene or a genetic or physiological regulatory switch that renders the intended activity absent or conditionally absent.

The term "degrading" refers to the hydrolysis of covalent bonds within the oligonucleotide, and such bonds include the glycosidic bonds between the nucleic acid base and the sugar moiety and/or the ester bonds between the phosphate backbone and the sugar moiety.

The term "host cell(s)" refers to both single cellular prokaryote and eukaryote organisms such as bacteria, yeast, and actinomycetes and single cells from higher order plants or animals when being grown in cell culture.

The term "host cell nucleic acid" refers to both endogenous or native nucleic acid and recombinant nucleic acid.

The term "non-specific amplification" refers to amplification products that result from primers hybridizing to sequences other than the target sequence and then serving as a substrate for primer extension. The resulting products are not the intended products of the amplification process.

The term "specific" when referring to a particular nucleoside glycosylase (nucleic acid N-glycosylase) denotes the relationship between glycosylases and their corresponding substrates. Thus, the phrase "specific nucleoside N-glycosylase" embraces all glycosylases and the phrase "specific modified nucleosides" refers to those substrates that are recognized by corresponding glycoslyases.

The term "sterilizing" or "restricting" refers to the elimination of carryover or contaminating nucleic acid from prior amplification reactions or from ancillary nucleic acid introduced by the amplification system reagents. Sterilization (restriction) of the carryover nucleic acid is a accomplished by removal of certain bases and cleavage of the polynucleotide backbone. Sterilization can occur either before placing the target nucleic acid into an amplification reaction tube or after introduction of the target nucleic acid to the various reagents responsible for amplification.

The term "thermostable" typically refers to an enzyme that retains activity even after exposure to temperatures necessary to separate two strands of double-helical nucleic acid.

The term "unconventional" or "modified" when referring to a nucleic acid base, nucleoside, or nucleotide includes modification, derivations, or analogs of conventional bases, nucleosides, or nucleotides that naturally occur in a particular polynucleotide (e.g. DNA [dA, dG, dC, dT] or RNA [A, G, C, U]). Uracil is an unconventional or modified base in DNA but is a conventional base in RNA.

The term "vector" refers to both cloning plasmids and plasmids or DNA fragments that are capable of directing the expression of a protein by virtue of a DNA sequence encoding the protein being operatively linked to a promoter capable of being recognized by the host cell. The vector may be extrachromosomal in the host cell or be incorporated in whole or in part into the genome of the host cell.

This invention relates generally to improvements for amplification reactions where non-specific amplification and/or carryover contamination is a problem. This invention provides means for improving the specificity of amplification and preventing carryover contamination, means for producing recombinant proteins substantially free of contaminating host nucleic acid, means for producing and purifying a preferred glycosylase, and stabilized formulations of the glycosylase.

I. Carryover Contamination

There are several known systems for amplifying nucleic acids. These amplification systems are extremely sensitive methods for increasing the number of copies of a nucleic acid segment. Whenever amplification proceeds at a geometric rate, non-specific amplification and contamination of a reaction vessel even at extremely low levels can be of substantial concern.

In particular, the non-specific amplification that occurs in amplification reaction mixtures incubated at temperatures below the specific hybridization temperature preferred for primer or oligomer binding is a serious problem. Because most amplification reaction mixtures are completely assembled at room temperature and then heated to or above the preferred hybridization temperature, the problem of non-specific amplification is frequently encounter. The present invention provides a method for reducing non-specific amplification in amplification systems that utilize polymerase-mediated primer extension.

In addition, aerosol contamination of subsequent amplification reactions by the product generated by earlier amplification reactions is a significant problem. Thus, scrupulous care is required to ensure that all reagents and reaction vessels are devoid of contamination from prior amplification reactions, as this contamination might give rise to false positives. This invention eliminates carryover contamination and so provides increased confidence in the results from diagnostic and other assays relying upon nucleic acid amplification.

The performance of this invention requires a multiplicity of steps, each of which can be performed in a variety of ways. Some steps depend upon the circumstances of the process, and some are non-critical variations dependent upon convenience and economy. The following details provide those of skill with sufficient information to carry out the invention without undue experimentation. Optimization of the invention for particular purposes will require routine experimentation to determine preferred conditions.

In brief, this aspect of the disclosed invention requires the isolation of sample or target nucleic acid, the amplification of the target, the detection of the amplified products and, if desired, the removal of carryover templates in reactions about to undergo amplification. Each step is described in detail below.

A. Isolation of Target Nucleic Acid

Amplification systems such as PCR require a target nucleic acid in a buffer compatible with the enzymes used to amplify the target. The target nucleic acid can be isolated from a variety of biological materials including tissues, body fluids, feces, sputum, saliva, plant cells, bacterial cultures, and the like.

In general, the nucleic acid in the sample will be a sequence of DNA, most usually genomic DNA. However, the present invention can also be practiced with other nucleic acids, such as messenger RNA, ribosomal RNA, viral RNA, or cloned DNA. Suitable nucleic acid samples include single or double-stranded DNA or RNA. Those of skill in the an recognize that, whatever the nature of the nucleic acid, the nucleic acid can be amplified merely by making appropriate and well recognized modifications to the method being used.

To amplify a target nucleic acid sequence in a sample, the sequence must be accessible to the components of the amplification system. In general, this accessibility is ensured by isolating the nucleic acids from a crude biological sample. A variety of techniques for extracting nucleic acids from biological samples are known in the art. For example, see those described in Maniatis et al., *Molecular Cloning: A Laboratory Manual* (New York, Cold Spring Harbor Laboratory, 1982); Arrand, Preparation of Nucleic Acid Probes, in pp. 18–30, *Nucleic Acid Hybridization: A Practical Approach* (Ed Hames and Higgins, IRL Press, 1985); or, in *PCR Protocols*, Chapters 18–20 (Innis et at., ed., Academic Press, 1990).

Whole cell nucleic acid extraction procedures typically involve an initial disruption with phenol, phenol/chloroform, or guanidinium salts, followed by an alcohol precipitation. Alternative extraction procedures using proteinase K and non-ionic detergents may also be used. Genomic DNA may be obtained from a whole cell nucleic acid extraction by using RNase before further alcohol precipitation. If rapid processing of sample is desired, the nucleic acid need not be purified prior to amplification, i.e., if the sample is comprised of cells, particularly peripheral blood lymphocytes or amniocytes, lysis and dispersion of the inncellular components may be accomplished by suspending the cells in hypotonic buffer or by boiling the cells.

Where the amplification system is PCR, TAS, 3SR, or LAR, the targets are nucleic acids and are isolated as described above. In LAR, oligonucleotides are joined (e.g., ligated); the only buffer condition limitations for LAR are those required to maintain the enzymatic activity of the ligase enzyme. Where the amplification system relies upon the replication system of bacteriophage Q$\beta$, the system will replicate RNA probe sequences rather than target sequences. The targets can be nucleic acids as described above or they can be proteins or other biologicals to which a ligand/antiligand system is applicable. The "probes" are then attached to one member of the binding pair and replicated by the Q$\beta$ polymerase. Isolation procedures for non-nucleic acid targets are as varied as the targets and are non-critical aspects of this invention understood by those of ordinary skill.

B. Amplification Systems

The systems described below are practiced routinely by those of skill in the relevant art and have been described in detail by others and so are merely summarized below. This invention is not limited to any particular amplification system. As other systems are developed, those systems can benefit by practice of this invention. Any amplification system based upon nucleic acid polymerase, nucleic acid ligase, or "replicase nucleic acid extension" will benefit from the disclosed invention. A recent survey of amplification systems was published in *Bio/Technology* 8:290–293, April 1990, incorporated herein by reference. The following four systems are described below for the convenience of those not familiar with amplification systems and to provide an understanding of the breadth of the present invention.

POLYMERASE CHAIN REACTION PROCEDURE

The PCR process is well known in the art (see U.S. Pat. Nos. 4,683,195; 4,683,202; and 4,965,188, each of which is incorporated herein by reference), and components are available commercially through Perkin-Elmer/Cetus Instruments (PECI) of Norwalk, Conn., which sells PCR reagents and instruments. PCR involves hybridizing single-strands of target nucleic acid with primers that flank a target sequence. The primers are then extended to form complementary copies of the target strands, and the cycle of denaturation, hybridization, and extension is repeated as many times as necessary to obtain the desired amount of amplified nucleic acid.

The target nucleic acid in the PCR sample is first denatured (assuming the target nucleic acid is double-stranded) to begin the amplification process. Because simply heating some samples results in the disruption of cells, isolation of nucleic acid from the sample can sometimes be accomplished in conjunction with strand separation. Strand separation may also be induced by a helicase, an enzyme capable of exhibiting strand separating activity. For example, the enzyme product of the RecA gene has helicase activity in the presence of ATP. The reaction conditions suitable for strand separation by helicases are known in the art (see Kuhn Hoffman-Berling, 1978, *CSH-Quantitative Biology* 43:63:and Radding, 1982, *Ann. Rev. Genetics* 8 16:405–436).

As noted above, strand separation may be accomplished in conjunction with the isolation of the sample nucleic acid or as a separate step. Those of skill in the an recognize that strand separation is carried out prior to annealing primers and synthesizing primer extension products. The primers are designed to bind to opposite strands and flank the target sequence. As the primers are extended using DNA polymerase, the extension products provide copies of the original target sequence and can in turn act as target sequences.

Template-dependent extension of primers in PCR is catalyzed by a polymerizing enzyme in the presence of adequate amounts of four deoxyribonucleoside triphosphates (dATP, dGTP, dCTP, dTTp, and modified bases) in a reaction medium comprised of the appropriate salts, metal cations, and pH buffering system. Suitable polymerases are enzymes known to catalyze template- and primer-dependent DNA synthesis. For example, if the template is RNA, a suitable polymerase to convert the RNA into a complementary DNA (cDNA) sequence is reverse transcriptase (RT), such as arian myeloblastosis virus or moloney murine leukemia virus RT. In addition, DNA polymerases from *Thermus aquaticus* and *Thermus thermophilus* have reverse transcription activity and are useful in this invention. (See for example U.S. Pat. No. 5,322,770 U.S. Ser. No. 455,967, filed on Dec. 22, 1989, now abandoned, and Ser. No. 585,471, filed Sep. 20, 1990, now abandoned, and PCT Application No. US 90/0764 1, filed Dec. 21, 1990, each of which is incorporated herein by reference.)

Once the target for amplification is DNA, suitable polymerases include, for example, *E. Coli* DNA polymerase I or its Klenow fragment, $T_4$ DNA polymerase, and Taq DNA polymerase, a heat stable DNA polymerase isolated from *Thermos aquaticus* and commercially available from PECI. See also U.S. Pat. No. 4,889,818, incorporated herein by reference. The latter enzyme is widely used in the amplification and sequencing of nucleic acids. The reaction conditions for using DNA polymerases are known in the art and are described, for example, in EP No. 258,017, and in Maniatis et al., *Molecular Cloning: A Laboratory Manual*, supra. See also U.S. Pat. No. 4,965,188, incorporated herein by reference.

The PCR method can be performed in a step-wise fashion, where after each step new reagents are added, or in a batch fashion where all of the reagents are added prior to a given number of steps. For example, if strand separation is induced by heat, and the polymerase is heat-sensitive, then the polymerase will have to be added after every round of strand separation. However, if, for example, a helicase is used for denaturation, or if a thermostable polymerase is used for extension, then all of the reagents may be added initially. Alternatively, if molar ratios of reagents are of consequence to the reaction, the reagents may be replenished periodically as they are depleted by the synthetic reaction.

During the PCR process, the temperature should be controlled so that strand separation and primer annealing and extension occur optimally. The extension step of the PCR process is preferably catalyzed by a heat-stable polymerase and carried out at an elevated temperature. The denaturing temperature is one at which the target nucleic acid strands are separate or primarily single-stranded. The reaction temperature is then reduced to a temperature which permits primer to anneal to the template strands and allows a reasonable rate of polymerization by the thermostable polymerase. Strand separation is usually achieved by heating the reaction to a sufficiently high temperature for an effective time to cause the denaturation of the duplex but not to cause an irreversible denaturation of the thermostable polymerase (see EP No. 258,017).

Those skilled in the art will know that the PCR process is most usually carried out as an automated process with a thermostable enzyme. In this process, the reaction mixture is cycled through a denaturing temperature range, a primer annealing temperature range, and a primer extension temperature range. A machine specifically adapted for use with a thermostable enzyme is disclosed more completely in EP No. 236,069 and is commercially available from PECI.

LIGASE AMPLIFICATION (OR CHAIN) REACTION (LAR OR LCR)

The ligase amplification reaction (LAR), like PCR, uses repetitive cycles of alternating temperature to accomplish the exponential increase in the desired target region. Following the denaturation of the template DNA double-helix, the procedure initiates with the DNA ligase catalyzed joining of two synthetic oligonucleotides complementary to adjacent regions on one of the strands. In addition, two other oligonucleotides complementary to the opposite strand can also be joined. After another denaturation step, the original template strands and the two newly joined products serve as templates for ligation. If doubling of the targeted region resulted at each cycle, an exponential amplification would result.

Investigators have begun exploring the use of a thermostable enzyme for catalysis of LAR in an analogous manner to the switch from the *E. coli* to the *T. aquaticus* DNA polymerase for PCR. Double or single stranded DNA can serve as a template for LAR. Ligases for RNA are also known but are usually not template-dependent. Ligases may join DNA oligonucleotides on an RNA template, thereby circumventing the necessity of a cDNA synthesis step in LAR. Alternatively after a reverse transcriptase step, single or double stranded RNA may also serve as a template for amplification using DNA ligase. See *Genomics* 4:560–569, 1989.

The LAR procedure has the potential to generate large numbers of copies of a target sequence. Because ligated product can serve as templates themselves, errant ligated molecules may cause amplification in a reaction that otherwise lacks these sequences. The "restriction" strategy described for PCR employing the incorporation of unconventional bases both to distinguish between newly synthesized product and provide the differential lability of the PCR product due to the nature of the unconventional base can also be used for LAR. However, the unconventional bases would be present in the synthetic oligonucleotides for LAR. Synthetic oligonucleotides can be prepared containing several unconventional bases. As an example, deoxyuracil (deoxyuridylate) can replace thymine (deoxythymidylate) in the oligonucleotides intended for joining.

Restriction of the errant LAR products can be accomplished in at least two ways. First, all components of the reaction, except the synthetic oligonucleotides, are treated with uracil-DNA glycosylase. The glycosylase is inactivated at elevated temperatures, and the synthetic oligonucleotides planned for amplification added prior to initiating the LAR. In a second strategy, the synthetic oligonucleotides would contain 3' terminal uracil bases. Because uracil-DNA glycosylase has a significantly impaired ability to remove a uracil located at the 3' terminal position of an oligonucleotide, all components of the LAR reaction, including the oligonucleotides planned for joining, would be treated with glyeosylase prior to inactivating the glycoslyase enzyme and cycling to achieve amplification of the targeted sequence. After joining, the terminal residue is an internal residue and becomes a substrate for the appropriate glycosylase. Just as several unconventional bases can serve for the PCR restriction reaction, multiple unconventional bases can also serve in this capacity for LAR.

Oβ Replication System

Another amplification scheme exploits the use of the replicase from the RNA bacteriophage Qβ. In this amplification scheme, a modified recombinant bacteriophage genome with a sequence specific for the targeted sequence is initially hybridized with the nucleic acid to be tested. Following enrichment of the duplexes formed between the bacteriophage probe and the nucleic acid in a sample, Qβ replicase is added, which, upon recognizing the retained recombinant genome, begins making large numbers of copies.

The Qβ system does not require primer sequences or a heat denaturation step as with the PCR and LAR amplification systems. The reaction occurs at one temperature, typically 37° C. The preferred template is a substrate for the Qβ replicase, midvariant-1 RNA. A very large increase in the templates is achieved through the use of this system.

The probe can be any ligand or anti-ligand where the analyte is the binding partner. The RNA is bound to the probe using techniques well known in the art. Uridine is not a preferred nucleoside in this system. The preferred modified base is 7-methyl GTP, and the resulting modified nucleotide-containing RNA can be degraded by heat and treatment to open the imidazole rings. See *J. Biol. Chem.* 245(3):447–482, 1970, and *Biochemistry* 20:5201–5207, 1981, each of which is incorporated herein by reference.

If the Qβ replicase is unduly sensitive to the restriction/sterilization process, one can simply add the replicase to the amplification system after sterilization. Additionally, use of recombinant techniques makes possible modification of the replicating RNA to incorporate nucleotide sequences that specifically hybridize to either nucleic acid analyte or probe through complementary binding. A review of this amplification system can be found in the International Patent Application Pub. No. WO 87/06270 and in Lizardi et al., 1988, *Bio/Technology* 6:1197–1202.

SELF SUSTAINED SEQUENCE REPLICATION (3R)

The 3SR system is a variation of an ill vitro transcription based amplification system. A transcription-based amplification system (TAS) involves the use of primers that encode a promoter to generate DNA copies of a target strand and the production of RNA copies from the DNA copies with an RNA polymerase. See, e.g., Example 9B of U.S. Pat. No. 4,683,202 and EP No. 310,229. The 3SR System is a system which uses three enzymes to carry out an isothermal replication of target nucleic acids.

The system begins with a target of single-stranded RNA to which a DNA primer that encodes a promoter (i.e., for T7 RNA polymerase) is bound. By extension of the primer with reverse transcriptase, a CDNA is formed, and RNAseH treatment frees the cDNA from the heteroduplex. A second primer is bound to the cDNA and a double stranded cDNA is formed by DNA polymerase (i.e., reverse transcriptase) treatment. One (or both) of the primers encodes a promoter, so that the double-stranded cDNA is transcription template for RNA polymerase.

Transcription competent cDNAs yield antisense RNA copies of the original target. The transcripts are then convened by the reverse transcriptase to double stranded cDNA containing double-stranded promoters, optionally on both ends in an inverted repeat orientation. These DNAs can yield RNAs, which can reenter the cycle. A more complete description of the 3SR system can be found in Guatelli et at., 1990, *Proc. Natl. Acad. Sci. USA.* 87:1874–1878, and EP No. 329,822, both of which are incorporated herein by reference.

C. Incorporation of Modified Nucleotides into the Amplification Products

For amplification systems such as the basic PCR method or the Qβ replicase system where polymerase activity is a part of the amplification process, one generally uses four conventional (natural) nucleoside triphosphates, dNTPs, (e.g., dATP, dCTP, dTTP, and dGTP for DNA polymerases; and, ATP, CTP, UTP and GTP for RNA polymerases). By incorporation of unconventional nucleotides, the amplified products have properties that can be exploited to reduce non-specific amplification and/or eliminate carryover problems.

The term "unconventional nucleosides" refers to unnatural or analog type nucleoside triphosphates that can participate in the amplification process, i.e., be polymerized in a template dependent mariner into the amplified products. The resulting newly synthesized polynucleotides themselves generally serve as templates for further amplification. Unnatural forms of modified nucleotides include alkylated nucleotides and nucleotides modified by alkylhydroxylation. Specific examples of modified nucleotides include but are not limited to N-7 methylguanine, deoxyuridine, deoxyinosine, deoxy 5,6-dihydroxythymine (from OsO4 treated DNA), 5',6'-dihydroxydihydrothymine, and deoxy 3'-methyladenosine.

Unconventional nucleosides also comprise natural forms of nucleosides. The most common natural deoxyribose bases are adenine, cytosine, guanine, and thymine. Uracil and hypoxanthine are natural bases, but, for purposes of the present invention, their corresponding nucleosides are unconventional nucleosides when incorporated into DNA.

For PCR, TAS, or 3SR, one can optionally incorporate modified bases into the primers. This ensures complete degradation of the amplified product. When uracil N-glycosylase (UNG) is used to sterilize a PCR, TAS, or 3SR, the primers that are used should contain dA nucleotides near the 3' termini so that any primer-dimer generated in the reaction is efficiently degraded by UNG as well as any dU-containing PCR products. The further a dA nucleotide is from the 3' terminus of the primer, the more likely that partially degraded primer-dimer molecules may serve as templates for a subsequent PCR amplification. Production of primer-dimer can compromise the amplification of the desired target. Alternatively, or if primers cannot be selected with dA residues near the 3' termini, primers with 3' terminal or internal dU nucleotides should be used. Terminal dU nucleotides are not substrates for UNG and thus unextended primers with 3' dU termini will not be degraded by UNG. Primers that contain internal modified nucleotides must be added, of course, after the initial sterilization step. Biotin-dUMP derivatives are not substrates for UNG.

Thus, a preferred modified nucleoside for PCR and LAR is deoxyuridylate (2'-deoxyuridine 5'-triphosphate). This nucleoside can be directly added to the PCR mixture as dUTP, or an oligonucleotide containing this residue can be used in an LAR mixture. Of course, the use of dUTP (or any other modified nucleoside) assumes that the nucleic acid to be amplified will require dUTP (or the modified nucleoside present in the reactions) for amplification. Although many PCR systems are amplified efficiently when an equimolar (relative to the other dNTPs) concentration of dUTP (in place of dTYP) is present in a standard PCR mixture, some PCR systems require increasing the dUTP concentration 2 to 5 fold (e.g., 400 to 1,000 $\mu$M) for optimal amplification efficiencies. One can also use a mixture of dUTP and dTYP (or mixtures of any modified and corresponding conventional nucleoside) in the amplification step of the present method. One should increase $MgCl_2$, on an equimolar basis, when an increase in dUTP is required. For instance, a PCR buffer comprising 1 mM dUTP and 2.5 mM $MgCl_2$ provides good amplification efficiencies. In some PCR systems, the level of amplification obtained even with 1,000 $\mu$M dUTP may be less than the level obtained with 200 $\mu$M dTTP. However, one can also elongate the extension step and/or increase the amount of polymerase enzyme to increase the efficiency of PCR amplification when dUTP is Used as the unconventional nucleoside.

As noted above, the optimal magnesium chloride concentration may vary in a PCR, depending on the total dNTP concentration and on the primers, templates, and polymerase used in the reaction. In most eases, a final concentration of $MgCl_2$ in the range of 1.0 to 5.0 mM in the reaction mix will work well. The addition of UNG does not affect the $MgCl_2$ optimum of a PCR amplification, and magnesium ion is not required for optimal UNG activity.

Key criteria for consideration in the selection of an unconventional nucleoside or nucleotide in the present method include the ability of the nucleotide to participate in the polymerase process, pair specifically with a natural nucleotide, and serve effectively as a template for amplification when incorporated into a nucleic acid strand. Where unconventional nucleosides are being incorporated into amplification products, routine titration experiments may be necessary to optimize reaction conditions. The parameters that are varied include, but are not limited to, the concentration of divalent cations, pH range, concentration of enzyme (polymerase), concentration of unconventional nucleoside, the addition of the natural nucleoside for which the unconventional nucleoside is inserted, time of each cycle, and temperature. Reaction conditions for incorporating a variety of unconventional nucleosides into DNA using *E. coli* DNA polymerase I are known and have been summarized in DNA Replication by Arthur Kornberg, 1980 (W. H. Freeman and Co., San Francisco, Cali.), at Table 4.4 on page 119. These analogs can also function in a similar fashion as conventional nucleotides in protein-nucleic acid interactions. See Ward el al., *J. Biol. Chem.* 258(24):15206–15213.

Where an amplification system, such as LAR, does not require an in vitro synthesis of nucleic acid by polymerase activity, the unconventional nucleosides may be introduced directly into the substrate oligonucleotides during chemical synthesis of the oligonucleotides or by chemical modification after synthesis. The key consideration for application of the present method in an LAR system is the ability of the modified nucleotides to participate in the complementary binding of the ligase substrate oligonucleotides to its binding target template. Where an unconventional nucleotide might interfere with the ligase activity, one should incorporate the modified nucleotides into the oligonucleotides to be ligated an acceptable distance from the site of ligation.

D. Analysis and Detection Systems

Analysis of the amplified products may be achieved by a variety of means depending upon the information required. The nucleotide sequence of amplified products can be obtained using standard procedures such as the protocol described by Innis et al., 1988, *Proc. Natl. Acad. Sci.* 85:9436–9440. The PCR products can be sequenced directly (Saiki et al., 1988, *Science* 239:487–491) or indirectly by first cloning the products and replicating them in an appropriate cell.

For diagnostic situations where sequence data is not necessary, the presence or absence of an amplified product may be sufficient information. Molecular sizing technology, most preferably gel electrophoresis, can be used for this purpose. In particular, agarose and/or acrylamide gel electrophoresis are preferred means for analyzing and detecting amplified products. (Scharf et al., 1986, *Science* 233:1076–1078).

The detection of the amplified products can be accomplished by direct visualization of gels or by using nucleic acid hybridization signal probes. Examples of hybridization assays include the Southern procedure, dot blot, and homogeneous hybridization assays where both the target and signal oligonucleotides are free in solution. See, e.g., U.S. patent application Ser. Nos. 491,210, filed Mar. 9, 1990 and ; 347,495, filed. May 4, 1989, now abandoned; U.S. Pat. No. 5,210,015 each of which is incorporated herein by reference.

The signal probes can be labeled by any of the methods known in the art. Radioactive, ligand, and enzyme labels are preferred. Most preferred are labels that eventually allow the production of a colored product, i.e., such labels as horseradish peroxidase and alkaline phosphatase. Color development can be accomplished by a variety of means using a variety of known substrates. Preferred methods for horseradish peroxidase include using tetramethylbenzidine as described in *Clin. Chem.* 33/8:1368–1371 (1987). Art alternative detection system is the Enhanced Chemiluminescent detection kit [ECL] commercially available from Amersham (Arlington Heights, Ill.). The kit is used in accordance with the manufacturer's directions.

E. Reduction of Non-Specific Amplification

An important aspect of the present invention relates to improved primer extension-based amplification systems. Such systems can be improved dramatically by the incorporation of a modified nucleoside triphosphate and corresponding glycosylase into the amplification reaction mixture. The improvement is the reduction of nonspecific amplification, or non-specific primer extension.

Non-specific primer extension occurs when a primer binds to a sequence other than the intended target sequence and then is extended. Typically, this other sequence is a sequence to which the primer is not exactly complementary but does have some significant degree of complementarity. For any primer, there is generally a hybridization temperature at which binding of primer to exactly complementary sequences is favored overwhelmingly to binding of primer to non-complementary sequences. Below this temperature, however, a given primer can hybridize, especially in complex mixtures of nucleic acid, such as a genomic DNA sample, to a number of relatively non-complementary sequences, even to the exclusion of the target sequence.

Because amplification reaction mixtures are typically assembled at room temperature, and such mixtures are usually able to sustain polymerase activity at room temperature, and because the optimum temperature for specific hybridization of primer to target sequence is, as a general rule, significantly above room temperature, non-specific amplification is a common problem in primer-based amplification systems. In some systems and with certain samples, non-specific amplification products can be the predominant product of an amplification reaction.

The present invention provides a method for reducing non-specific amplification that comprises incorporating a modified nucleoside triphosphate and glycosylase specific for the modified nucleoside triphosphate into the reaction mixture, incubating the mixture at a temperature below the temperature set for primer annealing and below the denaturation temperature of the glycosylase for a period of time sufficient for glycosylase to degrade non-specific amplification products, inactivating the glycosylase, and then carrying out the steps of the amplification process. As primer-based amplification systems typically involve, or can withstand, incubation at temperatures to denature double-stranded nucleic acids, and because such temperatures denature glycosylases (at least temporarily; see below), the inactivating step of the method is quite easily carried out.

For primer-based amplification systems that utilize dUTP as the modified nucleoside triphosphate and UNG as the corresponding glycosylase, the incubation time and temperature for the degrading of non-specific amplification products is 45° to 60° C. for a period of 2 to 5 minutes. This method of reducing non-specific amplification is described in more detail in the Examples.

F. Elimination of Carryover Contamination

Another objective of this invention is to solve the problem of carryover contamination from previous amplifications. In the typical situation, amplified products from a previous amplification may be present in minor amounts in any amplification reaction. These products are available as templates and may affect the accuracy of, or the results from, subsequent amplification assays.

To eliminate the carryover of amplified product, one takes advantage of the properties inherent in the amplified product as a results of the introduction of the modified bases as described above in Sec. C. Typically, this involves the introduction of a sterilization (restriction) agent or physical condition capable of directly or indirectly hydrolyzing or inducing the hydrolysis of covalent bonds between the modified bases and the remainder of the nucleotide. Hydrolysis can also be directed to the glycosidic linkage between the base and the sugar producing an abasic site or directed to the 3'-5' phosphodiester linkage between the sugar phosphate backbone producing oligonucleotide fragments of the original amplified product or both. These hydrolyzed amplification products are no longer capable of acting as templates for subsequent amplification.

In addition, another advantage of this invention is that in the amplification systems described, degraded (fragmented) amplification products are incompetent primers (PCR) or probe substrates (LAR) for amplification. The degraded fragments have blocked 3' ends that prevent participation in either the polymerization or ligation steps of subsequent amplifications. Thus, the invention prevents carryover product from competing with the reaction components in subsequent amplifications by different means.

The sterilization (restriction) agent can be an enzyme reagent, a chemical, radiation (thermal, x-ray, or ultraviolet), or a combination of agents. Chemical reagents include alkaline or acidic conditions that are known to modify natural bases or to alter further analog bases such that glycosidic linkages become sensitive to subsequent degradation. For example, 7-methylguanine can be hydrolyzed at the glycosylamine bond, see J. Biol. Chem. 245(3):447–482 and Biochem. 20:5201–5207, supra.

The preferred sterilization agent for PCR and LAR is an enzyme and most preferred are DNA glycosylases. Glycosylases are DNA repair enzymes are found in a variety of living organisms. The enzymes were reviewed by Lindahl, 1982, Ann. Rev. Biochem. 51:61–87, and by Sancar and Sancar, 1988, Ann. Rev. Biochem. 57:29–67. Glycosylase genes have been identified and cloned. (J. Biol. Chem., 1984, 259:13723–13729 [E. coli] and J. Biol. Chem., 1989, 264:9911–9914 [human]). There are several glycosylases available for use in this invention. These include: uracil-DNA glycosylase (also known as uracil N-glycosylase or UNG), hypoxanthine-DNA glycosylase, 3-methyladenine-DNA glycosylase I, 3-methyladenine-DNA glycosylase II, hydroxymethyl uracil-DNA glycosylase and formamidopyrimidine DNA glycosylase. Illustrative glycosylases and corresponding substrates are shown in the table below.

| DNA Glycosylases | |
| --- | --- |
| Enzyme | DNA Substrate Containing |
| Uracil-DNA glycosylase | Urcil |
| Hx DNA glycosylase | Hypoxanthine (Hx) |
| 3-mA DNA glycosylase I | 3-methyladenine (3-mA) |
| 3-mA DNA glycosylase II | 3-methyladenine, 7-methylguanine or 3-methylguanine |
| FaPy DNA glycosylase | Formanudo-pyrimidine (FaPy) moieties |
| 5,6-HT DNA glycosylase | 5,6-hydrated thymine (5,6-HT) moieties |
| Urea DNA glycosylase | Urea moieties |
| PD DNA glycosylase | Pyrimidine dimers (PD) |
| 5-HmU DNA glycosylase | 5-hydroxymethyl uracil (5-HmU) |
| 5-HmC DNA glycosylase | 5-hydroxymethl cytosine (5-HmC) |

The most preferred DNA glycoslyase for purposes of the present invention is uracil N-glycosylase. The preferred UNG enzyme is an ultrapure, nuclease free, 25 kDa enzyme (EC 3.2.2) encoded by the E. coli uracil N-glycosylase gene and produced in recombinant host cells. The UNG enzyme can be isolated from a number of sources, however, as shown by the table below.

| | | | Uracil DNA Glycosylases | | | | |
|---|---|---|---|---|---|---|---|
| Source | Molecular Weight (kDa) | Cofactor Requirement | $K_m$ (dUMP in DNA) (M) | $K_1$ (uracil) (M) | pH Optimum | Preferential Substrate | Activators and Inhibitors (Other than Uracil) |
| E. coli | 24.5 | None | $4 \times 10^{-8}$ | $1.2 \times 10^{-4}$ | 8.0 | SS DNA | Inhibited by NaCl |
| B. subtilis | 24.0 | None | $1.1 \times 10^{-9}$ | | 7.3–7.8 | | Inhibited by heavy metals; stimulated by NaCl |
| M. luteus | 19.4 | None | $7 \times 10^{-8}$ | $3.2 \times 10^{-4}$ | 5.0–7.0 | SS DNA | Activated by spermidine; inhibited by spermidine at high concentrations |
| B. stearothermophilus | 28–30 | None | $4 \times 10^{-7}$ | | | | Inhibited by NaCl |
| Yeast | 27.8 | None | | | 7.5–8.0 | | Inhibited by $CaCl_2$; stimulated by NaCl |
| Calf thymus | 28.7 | None | $7 \times 10^{-7}$ | | 7.2–8.6 | DS DNA | Inhibited by NaCl, $MgCl_2$, $CaCl_2$, p-hydroxymercuribenzoate (PCMB), thymine, thymidine, and TMP |

Because *E. coli* UNG has activity below 55° C., the annealing temperature used for PCR amplification should be at or above 55° C. In this manner, degradation of newly synthesized dU-containing PCR products by residual UNG activity can be avoided when heat denaturation is used to denature the LING. In similar fashion, because *E. coli* UNG has the ability to renature after heat denaturation, after the final PCR cycle, the PCR mixtures in which UNG is present should be held at 72° C. until removed from the Thermal Cycler. Such reaction mixes should be stored at −20° C. or be added to an equal volume of chloroform (or extracted with phenol) to prevent any degradation of dU-containing PCR products by residual reactivated UNG.

Alternatively, one can use a temperature-sensitive UNG in the present method. Such UNG derivatives, which can be expressed by recombinant means, are described in Duncan et al., June 1978, *J. Bacteriology* 134:1039–1047, incorporated herein by reference. At Table 2 of Ms reference, several temperature-sensitive UNG enzymes are described, including UNG-6, which appears to be the most temperature-sensitive but may be unstable. UNG-7 is the least temperature-sensitive UNG enzyme shown in the paper. The use of a temperature-sensitive UNG in the present method as applied to PCR systems can avoid the problems, such as activity up to 55° C. and renaturation after heat denaturation, associated With the native UNG enzyme.

Chemical modification of the native UNG enzyme can also be used to prevent degradation of deoxyuridine-containing PCR product in the presence of UNG, which was added before PCR and which survived inactivation during thermal cycling. Two major modes exist to prevent the post-PCR survival of UNG: (a) specific chemical inactivation of the enzyme by reagents added after thermal cycling is complete; and (b) chemical modification of UNG before PCR to create an enzyme with similar catalytic activity to but greater thermal lability than unmodified enzyme.

Two classes of amino acid side chains on the UNG molecule are preferred targets for chemical modification to achieve either of these functional goals. The enzyme contains one thiol (cysteine side chain) that is highly reactive with organomercurials such as p-chloromercuribenzoate, maleimides such as N-ethyl maleimide, organohalide alkylating agents such as iodoacetate and iodoacetamide, and disulfides such as dithio dinitrobenzoic acid. The UNG enzyme contains ten aliphatic primary amines (nine lysine side chains and one amino terminus) that are highly reactive with carboxylic acid anhydrides like acetic, succinic, maleic, and S-acetyl mercaptosuccinic anhydrides, with imidate esters such as ethyl acetimidate, with imidate thioesters such as 2-iminothiolane (IT), with N-hydroxysuccinimide esters such as N-succinimidyl 3-(2-pyridyldithio) propionate (SPDP), and with a wide range of aldehydes and ketones. The methods for modifying protein thiol and amino groups with these reagents are well known in the biochemical art, as is a much larger list of modifying reagents.

In one mode, Post-PCR catalytic activity of UNG is blocked by adding to the reaction mixture, shorty after amplification is completed, a sufficient quantity of one of the thiol- or amine-modifying reagents to inactivate any UNG enzyme that survived thermal cycling. Thiol modification is preferred to amine modification, because UNG is the only thiol-containing material normally present in Taq-mediated PCR mixtures or other Taq polymerase buffers, unless a thiol-containing solvent is present in the reaction mixture. Amplification occurs perfectly well without thiol in the solvent. Nucleic acid bases contain aromatic amines which, although less reactive than aliphatic amines, might potentially consume amine-modifying reagents.

The most rapidly reacting modifying reagents are preferred over slower ones simply to minimize the post-PCR period during which residual UNG activity might degrade PCR product. For example, maleimides generally react with thiols more rapidly than organohalide alkylating agents. Also preferred are modifying reagents that spontaneously hydrolyze on a time scale not much longer than that required to inactivate UNG, so that they cannot possibly interfere with post-PCR processing such as sequencing. For example, organohalides and maleimides are hydrolyzable (the former more rapidly than the latter), whereas organomercurials are not. Within any class of modifying reagents of similar reactivity, bulkier reagents are preferred over ones with smaller molecular volumes and more highly charged reagents are preferred over more neutral ones, simply because increased bulk (usually associated with increased hydrophobicity) and increased charge are more likely to interfere with enzyme activity.

Post-PCR enzyme inactivation is inconvenient in requiring a separate process step in which all reaction tubes are opened, augmented with a controlled volume of modifying reagent, mixed, and closed again. This step increases the opportunity for cross-contamination of reaction mixtures from different tubes. Therefore, it is much preferred to modify UNG prior to PCR, most conveniently during manufacture, in a way which does not reduce enzyme activity during storage, even for periods of up to several years, in the 0°–50° C. temperature range, but which results in rapid and permanent inactivation during heating to the 60°–100° C. temperature range of thermal cycling. One can determine by standard biochemical means whether a particular chemical modification inactivates the enzyme in the lower temperature range or increases thermal lability in the higher range.

Especially preferred for increasing enzyme thermal lability are thiolating agents such as SPDP, IT, and S-acetylmercaptosuccinic anhydride (SAMSA), which add aliphatic thiols to amine reactive groups. An enzyme molecule carrying several covalently attached reactive thiols is likely, upon heating to 60°–100° C., to unfold into inactive conformations followed by oxidation of the thiols to disulfides which crosslink various portions of the unfolded polypeptide chain. These crosslinks help to prevent refolding into the catalytically active conformation upon cooling when amplification is complete.

IT modification replaces aliphatic amines with fully reactive aliphatic thiols. SPDP modification replaces aliphatic amines with disulfide-protected aliphatic thiols which are rapidly activated by adding a low concentration of a low-molecular weight thiol such as mercaptoethanol or (preferably) dithiothreitol. SAMSA modification replaces aliphatic amines with thioester-protected aliphatic thiols which are rapidly activated by adding a low concentration of a strong nucleophile such as hydroxylamine. The practical distinction among these three common thiolation modes concerns the storage stability of a thiolated enzyme and the need for a separate thiol activation step.

An IT modified enzyme might experience inactivating oxidation during prolonged storage between manufacture and use, whereas an SPDP- or SAMSA-modified enzyme should become oxidatively labile only when activated; the chemical activation might be accomplished at the end of storage just before use. Depending on the conformational mobility of the molecule and the exact locations of the single cysteine residue in UNG and the SPDP-modified amino groups, SPDP-modified UNG might undergo inactivating crosslinking during storage because the free cysteine thiol might react with an SPDP-generated disulfide. On the other hand, if such crosslinking does not occur during storage, it still might occur during thermal cycling. Then it would be necessary to activate the blocked thiols of SPDP-modified UNG before thermal cycling because the single cysteine side chain of UNG could react directly with a blocked thiol when the enzyme is unfolded at high temperature.

There are several ways to reduce the oxidative lability during storage of free thiols such as might be added by IT. One is to store the enzyme at the lowest practical pH, normally between 5 and 6, where "practical" means that acid-promoted unfolding does not inactive enzyme more rapidly than thiol crosslinking does. The other is to add a low concentration, preferably between $10^{-5}$ and $10^{-3}$M, of a chelator which is especially effective in retarding thiol oxidation by dissolved oxygen, a reaction catalyzed by trace contaminating ions of the redoxactive transition metals, principally Fe, Cr, and Cu. Because chelator and thiol structure control chelator protective efficacy in an interdependent manner, preferably several chelators are screened to determine which one is most effective. Although ethylenediamine tetraacetic acid (EDTA) commonly is used for this function, diethylenetriamine pentaacetic acid (DTPA) and cyclohexane diamine tetraacetic acid (CDTA) often are more effective.

Chelator protection of thiols during storage of thiolated UNG must not interfere with transition metal ion catalysis of inactivating UNG thiol oxidation during thermal cycling. There are several ways to promote this end. One is to store the thiolated UNG at a concentration much higher than use concentration with the lowest effective chelator concentration, so that dilution at time of use renders chelator too dilute to interfere. Another is to use a chelator which binds $Mg^{2+}$ sufficiently well that addition of the $Mg^{2+}$ required for PCR suffices to prevent chelator from inactivating all of the redoxactive transition metal ion. EDTA, CDTA, and DTPA all should meet this criterion. Deliberate addition before PCR of a very low concentration of a catalytic metal ion such as $Cu^{2+}$ might be needed to block the effect of variability in degree of transition metal ion contamination among samples. Finally, chelator used to protect thiolated UNG during storage might be added in the form of an insoluble chelating resin, which cannot easily be carded over from the UNG storage container to the PCR tube. Commercially available chelating resins include Chelex (Bio-Rad Laboratories).

UNG may present a special opportunity for specific modification of amino groups to increase thermal lability. As purified from *E. coli* in which UNG has been expressed at high level, the enzyme is eluted by ascending salt gradient from anion exchange matrices and by descending salt gradient from hydrophobic interaction matrices as two peaks, the latter (but not the earlier) one of which in each case possesses some sort of chemical blockage of the lysine at residue position 15 (from the N-terminal methionine coded by the genomic sequence; the isolated protein lacks this methionine). As there is little precedent for prokaryotic post-translational modification of lysine, the simplest explanation for such selective blockage is that the enzyme catalytic mechanism involves group transfer from the substrate to an active-site lysine to form a catalytic intermediate which subsequently is hydrolyzed to regenerate a free active-site lysine. The second chromatographic peak, which constitutes about ⅓ of all of the UNG protein in a bacterial lysate, would then represent the catalytic intermediate.

The fact that the two chromatographic peaks have equal catalytic activity requires that if lysine 15 is an active-site residue, its modification is reversible during catalysis. This condition is consistent with the hypothesis that the second chromatographic peak is a catalytic intermediate. If this hypothesis is correct, then the second chromatographic peak can be modified by amine-reactive reagents without destroying catalytic activity, That is, modification to increase thermal lability can be accomplished without reducing catalytic activity in the 0°–50° C. range. Furthermore, if the second but not the first chromatographic peak can be amine-modified without catalytic inactivation, it would be beneficial to screen reversible amine modifiers, well known in the biochemical field, for ones which specifically react with lysine residue 15. Preferred reversible amine modifiers are aldehydes and ketones; pyridoxal phosphate has served as an active site-specific amine modifier for some enzymes. A reagent which can modify the first UNG chromatographic peak to have the properties of the second peak would improve the economics of preparing UNG modified to increase thermal lability.

The chemical and other modifications described above with particular reference to the *E. coli* UNG enzyme are broadly applicable to any DNA glycosylase that has significant activity at or after exposure to elevated temperature. Each of the above DNA glycosylases is specific for respective modified bases. Each excises the base leaving an abasic site in a double- or single-stranded DNA. Glycosylases are typically low in molecular weight (about 18,000 to 31,000 daltons) and do not require cofactors such as divalent metal cations. In addition, glycosylases do not efficiently recognize nucleoside triphosphates as substrates, The mode of action is a hydrolytic cleavage of the glycosyl bond between the base and the sugar.

The reaction conditions to achieve high activity for the glycosylases vary in accordance with the glycosylase being used. For each of the above described enzymes, in vitro conditions have been disclosed for maintaining activity. For example, for 3-methyladenine-DNA glycosylase II, a buffer system of 70 mM Hepes-KOH (pH 7.8), 1 mM dithiothreitol, 5 mM EDTA was acceptable (*J. Biol. Chem.* 259(22):13723–13729, 1984). For uracil-DNA glycosylase, one may use a buffer system of 10 mM Tris-HCl (pH 8.0) and 1 mM EDTA (*Proc. Natl. Acad. Sci.* USA, 82:488–492, 1985).

For PCR, one prefers that the glycosylase function in the same buffer system in which the polymerase, typically thermostable, functions. These two classes of enzymes are relatively stable and active over a wide range of overlapping reaction conditions. As previously explained, routine titration experiments will readily provide those conditions which optimize the activity of both enzymes to achieve the desired amplification. Where the glycosylase is not compatible with the amplification buffers, one can pretreat the sample containing target nucleic acid with the glycosylase in a compatible buffer and then either precipitate the target nucleic acid and resuspend the target in an appropriate buffer or merely adjust the buffer by addition of the appropriate reagents.

In PCR, the polymerases are incapable of efficiently copying templates having abasic sites. No further treatment may be necessary to nullify any carryover product. However, the glycosylase treated products may be further treated by degradation means specific for nucleic acids containing abasic sites. These include enzymatic and chemical means.

As an example of enzymatic means, apyrimidinic and apurinic endonucleases (AP endonucleases) may be mused to degrade further the glycosylase treated DNA. AP endonucleases hydrolyze the phosphodiester bond 5' or 3' to an abasic deoxyribose in DNA. There are a number of AP endonucleases useful in this aspect of the invention. Specific examples include: *E. coli* endonuclease IV (*J. Biol. Chem.* 252:2802–2807, 1977) and endonuclease V (*J. Biol. Chem.* 252:1647–1653, 1977 and *Methods in Enzymology*, 65:224–231, 1980). AP endonucleases have been obtained from several types of eukaryotic cells including insects (*J. Biol. Chem.* 264:9911–9914, 1989), rats (*Eur. J. Biochem.* 118:195–201, 1981), HELA cells (*J. Biol. Chem.* 256:3405–3414, 1981), and human placenta (*J. Biol. Chem.* 257:13455–13458, 1982). The mammalian AP endonucleases resemble *E. coli* endonuclease IV and are described as a class II endonuclease.

Alternatively, the abasic sites are sensitive to chemical degradation which is accelerated by elevated temperatures. Treatment of the glycosylase-treated nucleic acid with alkaline reagents (buffers) having a pH of about 8.0 and above with optional gentle heating at or above 37° C. cleaves the abasic sites. The alkaline pH of typical PCR buffers and the elevated temperature of the initial denaturation step (>94° C.) of PCR are more than sufficient to result in abasic polynucleotide strand scission.

Thus, when the present invention is applied to PCR amplifications to render selectively PCR products susceptible to cleavage, one begins with the substitution of dUTP for dTTP in the PCR reaction mix. UNG is added to the PCR reaction mix, and a short room temperature incubation step is required prior to the start of the PCR. This allows time for UNG to excise the uracil in carried-over dU-containing PCR products should they be present in the reaction. The excised dU-containing PCR products are refractory to further PCR amplification because of the frequent stalling of DNA polymerases at the abasic sites and/or cleavage of the abasic polynucleotide strands due to the inherent alkaline and thermal liability of the resulting abasic linkage. Because UNG is active on single- and double-stranded DNA, the procedure works on dU-containing PCR products from standard, denatured, or asymmetric PCR amplifications. Ribouracil residues in RNA and dUTP are not substrates of UNG.

Because of the enormous amplification possible with the PCR process, small levels of DNA contamination, from previous PCR amplification reactions, samples with high DNA levels, and positive control templates, can result in product even in the absence of purposefully added template DNA. Although the present method is capable of degrading or eliminating large numbers of PCR product carryover copies, one should also use good laboratory practice to minimize cross-contamination from non-dU-containing PCR products or other samples. Briefly, the use of dedicated pipettes (preferably positive displacement pipettes), vessels, and solutions for DNA preparation, reaction mixing, and sample analysis is recommended. In addition, all reactions should be set up in an area separate from PCR product analysis.

A master mix of reagents (water, buffer, dNTPs [dATP, dCTP, dGTP, and dUTP], primers, AmpliTaq ® DNA polymerase, and UNG) for all samples can be prepared first, then aliquoted to individual tubes. Magnesium chloride and template DNA are then added. Using such mixes will minimize pipetting losses, increase accuracy, and reduce the number of reagent transfers.

Amplifications are typically performed in 100 μL of reaction mix in capped 0.5 mL polypropylene microcentrifuge tubes. Perkin-Elmer Cetus 0.5 mL GeneAmp ® Reaction Tubes provide the best heat transfer when using the Perkin-Elmer Cetus DNA Thermal Cycler, because of their uniform fit in the wells. Because DNA may stick to plastic and because nucleases are often found on surfaces, it may be preferable to use sterile, siliconized tubes and pipette tips.

One prepares a typical PCR amplification according to the present method as shown in table below.

| Component | Addition Order | Volume | Final Concentration |
|---|---|---|---|
| Sterile distilled water | 1 | variable | |
| 10× PCR Buffer II | 2 | 10 μL | 1× |
| dATP, 10 mM | | 2 μL | 200 μM |
| dCTP, 10 mM | 3 | 2 μL | 200 μM |
| dGTP, 10 mM | | 2 μL | 200 μM |
| dUTP, 20 mM | | 1–5 μL | 200–1,000 μM |
| Primer 1 | 4 | 1–5 μL | 0.2–1.0 μM |
| Primer 2 | 5 | 1–5 μL | 0.2–1.0 μM |
| AmpliTaq ® DNA polymerase | 6 | 0.5 μL | 2.5 Units/100 μL |
| UNG | 7 | 1 μL | 1 Unit/100 μL |
| 25 mM MgCl$_2$ | 8 | 4–16 μL | 1.0–4.0 mM |
| Experimental template | 9 | variable | <1 μg/100 μL |
| Total Mix | | 100 μL | |

Any combination of sterile distilled water and experimental template volumes can be used as long as the total volume of the reaction (including buffer, dNTPs, primers, enzymes, and MgCl$_2$ solutions) equals 100 μL. 10X PCR buffer II is 100 mM Tris-HCl, pH 8.3, and 500 mM KCl.

Depending on the level of potential dU-containing PCR product cross-contamination, the amount of UNG needed may vary, With a short incubation step (0–10 minutes at room temperature), 1 Unit/100 μL reaction is generally more than sufficient to preclude subsequent reamplification of high levels (1×10$^6$ copies) of dU-containing PCR product. If further optimization of the concentration of UNG is desired, concentrations in the range of 1.0 to 2.0 Units/100 μL have been shown to be effective.

One unit of enzyme is defined as the amount that releases 1 nmole of uracil from a dU-containing DNA template into acid soluble material per 60 minutes at 37° C. in a reaction mixture of 10 mM Tris-HCl, pH 8.3 (at room temperature); 50 mM KCl, and 100 pmoles dUMP substrate (dU-containing lambda PCR product, a mix of unlabeled and $^3$H-uracil-labeled), in a final volume of 50 μL. A 10 minute reaction time is used. The dU-containing 500 bp lambda PCR product is prepared by following the procedure for amplifying the Control Template provided with the GeneAmp ® PCR Reagent Kit (Perkin-Elmer Cetus), except that the mixture of dUTP and $^3$H-uracil-dUTP are substituted for dTTP.

After the addition of MgCl$_2$ and experimental template DNA, a 1 to 10 minute incubation at room temperature (18° C. to 22° C.) is conducted to allow UNG to excise uracil from any contaminating dU-containing PCR product from previous amplifications. More preferred, however, is a two-to-five minute incubation at 45° to 65° C. not only to eliminate carryover contamination but also to reduce non-specific amplification. The time of this incubation depends on the level of UNG used and the potential for primer-dimer formation in the PCR system. The room temperature incubation is followed with at least a 10 minute incubation at 95° C. before starting the PCR process. Incubation at 95° C. for at least 10 minutes is necessary to cleave the abasic dU-containing PCR product generated in the room temperature incubation, to inactivate UNG, and to denature the native DNA in the experimental sample. if a shorter incubation at 95° C. is used, UNG may not be completely inactivated, leading to degradation of newly synthesized dU-containing PCR product during the PCR process.

The time used for the UNG reaction may affect the subsequent PCR amplification efficiency. When 1 Unit/100 μL of UNG is used, a 10 minute incubation at room temperature will be sufficient to degrade millions of copies of cross-contaminating dU-containing PCR products. The concentration of UNG and the time of the incubation step necessary to prevent amplification of contaminating dU-containing PCR products depend on the PCR conditions necessary to amplify the particular DNA sequence and the level of contamination to be expected. In most cases, the general recommendations of using UNG at 1 Unit/100 μL reaction and incubation at room temperature for 10 minutes will be acceptable. If the PCR system is prone to primer-dimer formulation, a 10 minute incubation at room temperature may result in the preferential amplification of primer-dimer sequences instead of the desired target sequence. If primer-dimer amplification dominates the PCR, one should reduce the incubation time at room temperature with or without increasing the UNG concentration to 2 Units/100 μL reaction.

Optimal performance of the PCR process is influenced by choice of temperature, time at temperature, and length of time between temperatures for each step in the cycle. A typical cycling profile for utilizing UNG to degrade contaminating dU-containing PCR products from previous amplifications prior to PCR amplification of freshly added native DNA experimental templates is as follows: (a) 0 to 10 minutes of UNG incubation at room temperature; (b) 10 minutes of UNG inactivation at 95° C.; (c) 1 minute of DNA melting at 95° C.; (d) 1 minute of primer annealing at 55°–65° C.; (e) 1 minute of primer extending at 72° C.; (f) 1 minute of DNA melting at 95C; and steps (c)–(f) are repeated as many times as necessary to obtain the desired level of amplification. Because polynucleotides containing uracil have been shown to have lower melting temperatures than those with thymine, PCR might be performed at lower denaturation temperatures after the initial denaturation step, thereby increasing the amount of active polymerase enzyme present during later cycles.

The substitution of dUTP for dTTP in PCR amplification leads to the generation of PCR products containing dU instead of dT. Although this renders the dU-containing PCR products susceptible to degradation by UNG, most other properties of dU-containing PCR products, relative to dT-containing PCR products, are largely not affected. Thus, dU-containing PCR products will serve in an equivalent manner as dT-containing PCR products as hybridization targets; will serve as templates for dideoxy-terminated sequencing reactions; and can be cloned directly, if transformed into an UNG- bacterial host.

The recognition of dU-containing DNA by restriction endonucleases has also been studied. Depending on the specific endonuclease, there may be no effect of the substitution of dU for dT on enzyme activity (e.g., EcoRI and BamHI) or the dU-containing DNA is cleaved more slowly than tiT-containing DNA (e.g., HpaI, HindII, and HindIII). For other endonucleases, the effect of substituting dU for dT on enzyme activity will need to be examined empirically on an individual enzyme basis.

The use of PCR products containing exclusively uracil is not recommended for protein binding or site-specific recognition studies (e.g., operators and promoters, restriction endonucleases, or methylases). The absence of the C5 methyl group of thymine in the major groove, the face of the helix most frequently involved in proteinnucleic acid interactions, and/or distortion of the glycosidic bonds of the dA:dU (and adjacent) base pairs may impair recognition by proteins. If protein recognition is important, then one can use a mixture of dTTP and dUTP to mitigate this problem and yet retain the benefits of the present invention.

F. Kits

Any of the above amplification processes are amenable to being prepared in kit form. Such kits include various compartments, vials, or containers of the various components and reagents used to perform the assays. In general, amplification buffers containing the polymerase, ligase, or replicase and nucleic acid primers, templates, or nucleoside triphosphates can be joined in a stable mixture. In the preferred embodiment, the end user need only add the target to initiate amplification. However in many situations, the target nucleic acids are within bacterial or eukaryote cells and require a lysing step followed by a purification step before amplification can be initiated.

: In one kit for PCR with Taq DNA polymerase, the amplification buffer comprising Taq, glycosylase, and primers may be made magnesium free to maintain optimum stability. See U.S. patent application Ser. No. 481,501, filed Feb. 16, 1990, and incorporated herein by reference. The magnesium is needed for polymerase activity and must be added before PCR amplification is begun. One buffer that permits uracil-DNA glycosylase activity and preserves Taq DNA polymerase activity (until magnesium can be added) is 10 mM Tris-HCl at pH 8.0, 50 mM KCl, 2 mM EDTA, and 200 µM each dNTP.

Another preferred kit of the present invention comprises a vial of purified uracil N-glycosylase and a vial of dUTP. The UNG can be provided at a concentration of 1 Unit/µL in a 500 µL tube containing 100 µL of UNG in a storage buffer comprising 5% glycerol (w/v), 150 mM NaCl, 30 mM Tris-HCl, pH 7.5 (at room temperature), 1.0 mM EDTA (ethylenediamine-tetraacetic acid), 1 mM DTr (dithiothreitol), and 0.05% Tween 20 ®. The dUTP can be provided at a concentration of 20 mM in a 500 µL tube containing 320 µL of dUTP in glass-distilled water, titrated with NaOH to pH 7.0. The kit should be stored at −20° .C in a constant temperature freezer to maintain performance.

Those of skill in the an recognize that the kits of the present invention can contain various components of any of the amplification systems together with a glycosylase and/or modified nucleoside triphosphate. Each component can be provided in any suitable buffer or preparation.

II. Production of Recombinant Proteins in a Glycosylase Deficient Host Cell

As described in detail above in pan I of this disclosure, amplification systems are extremely sensitive to contamination. The amplification procedures described rely upon enzymes typically derived by overproduction in recombinant bacteria. One source of nucleic acid contamination in the amplification reagents is from these host cells. This is particularly problematic Where the target being amplified is a conserved sequence, such as subsequences of rRNA or structural genes that are conserved across genera or families. Such contamination is not a significant problem where the concentration of the target template will be in great excess over the endogenous contamination or where the nucleic acid derived from the host cells bears no sequence homology to the target template. However, where the template is a conserved sequence and present in low copy numbers, endogenous nucleic acid co-purified with the amplification reagents can be a significant problem.

This invention eliminates nucleic acid contamination, by first expressing the amplification reagents in glycosylase deficient mutant bacteria or other host cells. During purification, the amplification reagents, typically proteins or glycoproteins, are exposed to an appropriate glycosylase to hydrolyze intact nucleic acid which might be copurifying with the reagent. A preferred mutant is uracil-DNA glycosylase deficient E. coli. Such mutants permit the cell to maintain nucleic acid having modified nucleosides therein.

When viable, the mutant host cells contain significant proportions of nucleic acid with incorporated modified nucleotides. The cells are still able to replicate and express recombinant proteins. The proteins are expressed using conventional methods as described below. The proteins are purified using standard protein purification procedures well known in the an with the additional step of treatment with the appropriate glycosylase to cleave any residual host nucleic acid which might have copurified with the protein.

In the preferred embodiment, the host cell is deficient in both deoxyribouracil triphosphatase (dut-) and also mcil-DNA glycosylase (UNG-). The deficiency in dUTPase (in dut) permits an increase in the pool of deoxyuridine (deoxyribomcil) triphosphate (dUTP) which competes with thymidine triphosphate for incorporation into the host nucleic acid. The second deficiency (in UNG) precludes the host cell from eliminating the incorporated deoxyuracil bases.

Mutants of E. coli which are UNG or UNG and dut deficient are known. See U.S. Pat. No. 4,873,192; Proc. Natl. Acad. Sci. USA 75:233-237 (1975) and 82:488-492 (1985), which are incorporated herein by reference. E. coli strain BW313 is UNG- and dut-.

The cells deficient in the relevant glycosylase are transformed with recombinant vectors encoding amplification reagents using conventional recombinant genetic technology. For example, the methods for transforming E. coli to overexpress 3-methyladenine DNA glycosylase II are described in J. Biol. Chem. 259(22):13723-13729, and methods to overexpress thermostable DNA polymerase are described in EP No. 258,017, each of which is incorporated herein by reference.

When seeking to produce a glycosylase free of nucleic acid, one needs to avoid a host which is deficient in the glycosylase gene being introduced, as introduction would effectively restore the host to the wild type. In other words, one needs to select a glycosylase-deficient host that is deficient in a glycosylase other than the glycosylase being introduced and expressed. Should an appropriate glycosylase-deficient host be unavailable, glycosylase production could be placed under regulated control. By inducing overexpression at late log phase, one ensures that the host cells will have an abundance of unconventional bases present in their nucleic acid.

Alternatively, the activity of the induced specific glycosylase (e.g., UNG) can be inhibited by co-expression of a specific inhibitory activity (e.g., bacteriophage PBS2 uracil N-glycosylase inhibitor protein; see Wang and Mosbaugh, 1989, J. Biol. Chem. 264;1163-1171). Any carryover nucleic acid can be easily eliminated as templates for subsequent amplification by allowing the recombinant glycosylase to hydrolyze the unconventional bases present in the carryover. Alternatively, the glycosylase gene can be modified to encode an inactive protein after expression. Such an inactive protein is chemically restored to biological activity during or after the purification process. Such methods are known in the art and are typically used to express proteins that would otherwise be toxic to the host cells.

The protein compositions produced by this method are substantially free of intact nucleic acid. The term "substantially free" means that the amount of host cell nucleic acid (typically DNA) will be less than about 0.01% (W/W) of the total protein present and preferably less than about 0.001% (W/W) of the total protein present in the composition. In other terms, the amount of host cell nucleic acid is less than about 4 pg nucleic acid per 10 ng protein and preferably less than about 0.4 pg nucleic acid per 10 ng protein. In terms of therapeutic proteins used as human medicaments, the amount of intact nucleic acid is less than about 1.0 pg and preferably less than about 0.4 pg per dose of protein. The term "intact" means that the nucleic acid can function as a template for replication, transcription, or translation.

III. Production of Purified Uracil N-Glycosylase.

The examples below describe the recombinant expression of UNG and methods for purifying UNG from native and recombinant host cells. The present invention provides a purification method for UNG, which method comprises: (a) subjecting a cell extract containing UNG to anion exchange chromatography; and (b) subjecting the UNG containing fractions of step (a) to size-exclusion chromatography. In a different and preferred method, step (b) is replaced by a hydrophobic interaction chromatography step.

Step (a) is typically carried out in two steps, a salt gradient anion exchange extraction and an HPLC step. In an alternative method, step (a) is carried out with a pH-gradient anion exchange, which eliminates the dialysis step used when a saltgradient anion exchange method is used. The present invention also provides purification methods which allow baseline resolution of the two UNG peaks typically observed during chromatographic purification of UNG from E. coli cells. This resolution is provided by the use of shallow elution gradients for the anion exchange and hydrophobic interaction chromatography steps. Those of skill in the art recognize that although the examples below show the use of high pressure liquid chromatography steps, the methods are equally applicable to low pressure liquid chromatography steps.

The addition of nonionic surfactants or nonionic detergents to purified UNG provides increased stability and maintains UNG activity upon dilution. The term "nonionic polymeric detergents" refers to surface-active agents that have no ionic charge and that are characterized, for purposes of this invention, generally by a molecular weight in the range of approximately 100 to 250,000 daltons, preferably about 4,000 to 200,000 daltons, and by an ability to stabilize the enzyme at a pH of from about 3.5 to about 9.5, preferably from about 4 to 8.5. Examples of such detergents include those specified on pages 295-298 of McCutcheon's Emulsifiers and Detergents, North American edition (1983), published by the McCutcheon Division of MC Publishing Co., 175 Rock Road, Glen Rock, N.J. (USA), the entire disclosure of which is incorporated herein by reference.

Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straightchain alcohols, polyethylene glycol monooleate compounds, polysorbate compounds, and phenolic fatty alcohol ethers. More particularly preferred are Tween 20®, from ICI Americas Inc., Wilmington, Del., which is a polyoxyethylated (20) sorbitan monolaurate, and Iconol TM NP-40, from BASF Wyandotte Corp. Parsippany, N.J., which is an ethoxylated alkyl phenol (nonyl).

It will be apparent to those of skill that various substitutions and modifications may be made to the invention disclosed herein without departing from the scope and spirit of the invention. The following examples are provided for illustration purposes and should not be construed as a limitation of this invention.

EXAMPLE 1

PCR Amplifications Incorporating Uracil into Amplified Product and Treating with UNG PCR amplifications typically take place in 100 $\mu$l of 50 mM KCl, 10 mM Tris-HCl, at pH 8.3, and an amount of $MgCl_2$ that varies depending on the PCR primers employed in the amplification. The determination of optimum $MgCl_2$ concentrations is a routine empirical determination requiring titration experiments generally using between 0.65 to 5.0 mM $MgCl_2$ tested in two fold increments. The amount of Taq DNA polymerase also requires optimization. The amount of polymerase will vary from 1.25 to 5.0 units per reaction. The concentration of primer will generally vary from 0.1 $\mu$M to 1.0 $\mu$M of each primer. The nucleoside triphosphate (dNTP) concentrations are about 50 to 200 $\mu$M each (0.5 to 2 $\mu$l/100 $\mu$l of reaction mix of each 10 mM stock solution, dATP, dCTP, dGTP; and dUTP). UNG is added to the solution from a stock solution of 30 mM Tris-HCl pH 7.5, 1.0 mM EDTA, 1.0 mM dithiothreitol [DTT], 10% w/v Glycerol, and 0.05% Tween 20.

As noted above, small amounts of non-ionic detergent such as Triton X-100, Tween 20, or NP 40 are helpful to optimize UNG activity. The total amount of UNG can range from about 0.5 to about 100 ng/100 $\mu$L of reaction mixture and is more typically about 1.0 to about 10.0 ng/100 $\mu$L of reaction mixture and most typically between about 1 to about 2 ng/100 $\mu$L of reaction mixture.

A mastermix of all reagents (buffer, primers, dATP, dCTP, dGTP, dUTP, Taq DNA polymerase and UNG) is first combined into a microfuge tube at a 50 $\mu$l volume at concentration twice the desired final concentration. About 50 $\mu$l of mineral oil are dispensed into the tubes. The target DNA in 50 $\mu$l of liquid is then added to the tube, and the tube is closed. Glycosylase activity should be allowed to proceed for between 1 and 10 minutes to ensure complete hydrolysis of uridine-containing polydeoxyribonucleotides. In practice, however, complete hydrolysis usually occurs during reaction mixture preparation and initial heat treatment, so that no separate incubation step is required. The tube is briefly centrifuged in a microfuge to mix the aqueous solutions and float the oil. The thermocycler can be programmed to provide a 95° C. soak for 10 minutes to inactivate the UNG followed by a typical PCR thermal profile and the tubes placed in the block. This high temperature soak will effectively denature the UNG and permit the subsequent PCR amplification to proceed without detrimental effect from abasic sites in the amplified product arising from UNG activity. The tubes are then processed according to the particular PCR profile selected for the primer pair.

In the first protocol upon which the following example is based, the UNG was not stored in a buffer containing non-ionic detergent. In this example, a 186 bp region of the pol region of HTLV was amplified by the primers, SK432 and SKI 111, represented below as SK432/SK111. Suitable amplification conditions for the HTLV primer pair SK432/111 and an HTLV DNA containing plasmid as a target include the conditions as provided above with 2.5 units of Taq DNA polymerase, 1.25 mM MgCl$_2$, 0.5 μM (50 pmol) of each primer, and a PCR profile of 95° C. for 30 seconds, 50° C. for 25 seconds, 72° C. for one minute for 30 cycles followed by a 10 minute 72° C. extension.

For incorporating uracil into the amplified product of a 150 bp segment of the HIV-1 genome, the primer pair SK145/SK431 was used. The target was a plasmid containing the intact gag gene of HIV-1. The PCR mixture was a 100 μl volume plus 50 μL of light mineral oil. The reaction mixture contained 2.5 mM MgCl$_2$, 2.5 units of Taq polymerase, 10 mM Tris-HCl (pH 8.3), 50 mM KCl, 0.92 ng UNG, 200 μM each of dATP, dCTP, dGTP and dUTP (dTTP was used in place of dUTP in the controls), and 1,000 copies of target DNA.

The tubes were spun to float the oil. There was no set incubation period for the UNG to inactivate carryover products. The samples were soaked at 95° C. for 10 minutes to inactivate the UNG. The PCR profile was as follows: 95° C. for 30 seconds, 55° C. for 30 seconds, 72° C. for 1 minute for 30 cycles followed by 10 minutes at 72° C. Tubes were switched between temperatures without undue delay (programmed to be 1 second, but the transition actually takes longer).

The primers used in these amplifications are shown below. SEQ ID NO. 1 SK432 is a 28mer: 5'-ACCCATGTACCCTACAATCCCACCAGCT SEQ ID NO. 2 SK111 is a 24mer: 5'-GTGGTGGATTG-CCATCGGGTTTT SEQ ID NO. 3 SK145 is a 30mer: 5'-AGTGGGGGGACATCAAGCAGCCATG-CAAAT SEQ ID NO. 4 SK431 is a 27mer: 5'-TGCTATGTCAGTTCCCCTTGGTTCTCT Other PCR primers useful in the present method that can be used to amplify HIV sequences include PCR primer pairs CG22/CG21 and SK462/SK431. These primers (except for SK431, above) are shown below: SEQ ID NO. 5 CG22: 5'-AGTTGGAGGACAT-CAAGCAGCCATGCAAAU SEQ ID NO. 6 CG21: 5'-TGCTATGTCAGTTCCCCTTGGTTCTCU SEQ ID NO. 7 SK462: 5'-AGTTGGAGGACATCAAG-CAGCCATGCAAT As noted above, the PCR primers of the invention are characterized by the presence of 3' dU residues or by the presence of internal dU residues or both. A useful probe for detecting the presence of amplified SK145/SK431, CG22/CG21, or SK462/SK431 product is SK102, show below. SEQ ID NO. 8 SK102: 5'-GAGACCATCAATGAGGAAGCT-GACAAATGGGGAT

EXAMPLE 2

PCR Amplifications Incorporating Inosine into Amplified Product

Using the basic procedures described in Example 1, one can incorporate deoxyinosine into PCR generated product. The dITP incorporation benefits from elevated dNTP concentrations, with dITP at 0.5–1 mM and dCTP, dATP, and dTTP at 200 μM each. Taq DNA polymerase concentration should be increased to about 10 units per 100 μl reaction mix. The dITP is a modified nucleoside for purposes of the present invention. Treatment of ionsine-containing nucleic acids with hypoxanthine N-glycosidase results in the removal of the base from the inosine nucleotide.

EXAMPLE 3

PCR Cloning and high level expression of UNG in *E. coli*

Synthetic oligodeoxyribonucleotide primers DG205 and DG206 were used to amplify a DNA fragment containing a modified form of the *E. coli* UNG gene. "Upstream" primer DG205 is a 28-mer in which the twenty-two nucleotides at the 3'-end correspond to the *E. coli* UNG coding (+) strand sequence. The 5' end of DG205 encodes an NdeI restriction site (CA'TATG) as part of the (modified) UNG initiation codon. "Downstream" primer DG206 is a 31 mer in which the twenty-two nucleotides at the 3'-end are complementary to the 3'-end of the *E. coli* UNG noncoding (-) strand sequence. DG206 was designed to modify the natural TAA (Ochre) termination codon to a TGA (Opal) termination codon and introduce a BglII, restriction site (A'GATCT) immediately following and partially overlapping the translation termination codon.

Primers DG205 and DG206 (1 μM each) were used with *E. coli* genomic DNA (5 ng from *E. coli* K12 strain MM294), 50 μM each dNTP, 2 mM MgCl$_2$ in an otherwise standard PCR assay. The sequence of the primers is shown below. The cycling parameters were: 96° C. for 1 minute; step to 50° C. and hold 30 second; 1.5 min. ramp to 72° C. and hold 1 minute; and step to 96° C. This cycle was repeated four times and then repeated 25 times with a 60° C. (not 50° C.) anneal temperature. SEQ ID NO. 9 DG205 is a 28mer: 5'-CCGCATATGG-CTAACGAATTAACCTGGC SEQ ID NO. 10 DG206 is a 31mer. 5'-CGAGATCTCACT-CACTCTCTGCCGGTAATAC The 703 bp amplified DNA product was extracted with phenol/chloroform and precipitated with an equal volume of isoamyl alcohol from 2M ammonium acetate. The DNA fragment was digested with NdeI and bglII, and the resulting ~6.90 bp fragment was purified.

The UNG gene fragment was ligated with plasmid pDG 164 that had been digested with NdeI and BamHI and then treated with calf intestine phosphatase. Plasmid vector pDG164 is a ColEI-derived, ampicillin resistance conferring, 5.48 kb expression vector in which transcription of desired insert cassettes is initiated at the lambda PL promoter. Translation is initiated at a bacteriophage T7 gene 10 Shine-Dalgarno sequence, and transcription is terminated at the *B. thuringiensis* PRE. In addition, the primer RNA for ColEI initiation of DNA replication (RNAII) contains two cis-acting mutations which render initiation of ColEI DNA replication insensitive to regulation by ColEI RNAI at elevated temperature.

Plasmid pDG 164 and derivatives are maintained in *E. coli* host strain DG 116. DG 116 contains a defective lambda prophage (lysogenic only for cI and rex) which encodes a thermolabile repressor for the PL promoter. DG 116 was deposited on Apr. 7, 1987, with the American Type Culture Collection in Bethesda, Md, USA, under accession number 53606.

E. coli K12 strain DG116 was transformed with the ligated DNA and ampicillinresistant colonies were screened for the presence of the desired plasmid (6.15 kb). Candidate clones were further screened for induction (30° C. to 37° C.) of an expected ca. 26.5 kDa induced protein by SDS-PAGE. Candidate clones were further subjected to DNA sequence analysis (Sanger), and one of the clones containing the expected DNA sequence was designated pFC101.

Plasmid pFC101 in DG116 was deposited with American Type Culture collection in Bethesda, Md under the terms of the Budapest Treaty on Mar. 21, 1990, and has Accession Number 68265. The transformed strain DG116/pFC101 was further tested at 41° C. for induction of the E. coli UNG protein. There was no evidence of "refractile body" formation in the filamented cells. UNG protein accumulates to greater than 10% of the total cellular protein following four hours of induction at 41° C. The induced protein is soluble and not found in the 12,000 X G pellet fraction. The UNG gene coding sequence is described in *J. Biol. Chem.* 263(16):7776–7784 (1988).

UNG is purified from E. coli by fast disrupting the cells. About 1 to 5 gm of frozen cell pellet are thawed and suspended in 5× volume/weight 0.05M Tris-HCl, 1 mM EDTA, 0.1 mM DTT, pH 8.0. The cells are sonicated using a Branson Sonicator 350 with a ½" horn and tapered microtips with the duty cycle set to 50% and power to 7.0. The cell suspension container is set on ice and the sonicator probe is placed in the suspension. The suspension is sonicated for 4×60 seconds with at least 30 second rests between. The suspension is allowed to cool for at least 5 minutes and then sonicated 3 times for 60 seconds with 30 second rests.

Approximately 50 μL of the sonicate are saved and the rest is centrifuged for 10 minutes at 10,000×g, and then the supernatant is decanted. The pellet is resuspended in a volume of lysis buffer equal to the supernatant volume. The supernatant is filtered with a syringe using a 0.45 μm Acrodisc filter cartridge (Gilman Sciences, Acrodisc Disposable Filter Assembly, Product No. 4184, 0.45 μgin). The crude UNG can be stored −15° C.

To monitor recovery, one should analyze equal volumes of the unfractionated sonicate, filtered supernatant and resuspended pellet by SDS-PAGE. For example, one can use a Laemmli SDS-PAGE system (8–25% SDS-PAGE Phast Gel from Pharmacia Phast Gel System). After staining with a Coomassie stain, one can determine by visual inspection of the gel the approximate distribution of proteins between the pellet and the supernatant. If a significant fraction of the protein is still in the cell pellet, the pellet may be sent back through sonication steps set forth above.

The crude UNG preparations are next passed through a DEAE Sepharose column. The column is prepared with a bed volume of approximately 6 mL of DEAE Sepharose Fast Flow (Pharmacia, #17-0709-09). The column is equilibrated with at least 10 bed volumes of 50 mM Tris-HCl (Tris is hydroxymethyl aminomethane), 1 mM EDTA, 1.0M NaCl, pH 8.0, and then at least 10 bed volumes of 50 mM Tris-HCl, 1 mM EDTA, pH 8.0, at a flow rate of approximately 50 cm/hr. about 2 mL of the filtered cell supernatant are loaded onto the gel and eluted with 50 mM Tris-HCl, 1 mM EDTA, at pH 8.0, and fractions of approximately 0.5 mL are collected. The fractions are analyzed for absorbance at 280 nm. When a peak of A280 elutes, and absorbance begins to drop, the elution buffer is changed to 50 mM Tris, 1 mM EDTA, 0.2M NaCl, pH 8.0. When a second A280 peak elutes, the elution buffer is changed to 50 mM Tris-HCl, 1.0 mM EDTA, 1.0M NACl, pH 8.0 and elution is continued until a third peak elutes and the eluate absorbance returns to baseline.

The fractions of the second peak (the one which eluted with 0.2M NaCl) are pooled, the pool volume calculated by weight, assuming a density of 1.0, and A280 measured. The pooled fractions are dialyzed for 4 hr in at least 100 volumes of 20 mM Tris-HCl 1 mM EDTA, pH 8.0. The dialyzed pool may be stored at −15° C.

The semi-purified preparations are then subjected to anion-exchange HPLC. The following HPLC buffers are prepared: Buffer A=20 mM Tris-SO$_4$, pH 8.0, and Buffer B=20 mM Tris-SO$_4$, 0.5M Na$_2$SO$_4$, pH 8.0 (use a spectral grade of Na$_2$SO$_4$, e.g., Fluka #71969). A Bio-Gel DEAE-5-PW HPLC column (Bio-Rad Laboratories) is washed with at least 3 bed volumes of Buffer B and then equilibrated with at least 10 bed volumes of Buffer A, at a flow rate of 0.5 mL/min. Less than 0.5 mL of the dialyzed DEAE Sepharose pool are loaded onto the column and elution continued with Buffer A for 10 minutes, then a 0–40% gradient of Buffer B is run over 60 minutes. The eluate is monitored at 280 nm. Two large UNG-containing peaks should elute at between 35 and 45 minutes (total elapsed time from injection). The peaks are collected. The first peak, eluting at lower salt concentration is Peak 1. The fractions may be stored at 4° C.

The anion-exchange HPLC is repeated until all but approximately 50 μL of the dialyzed DEAE Sepharose sample has been processed. The Peak 1 fractions and the Peak 2 fractions are separately pooled. The volume of the pools is measured (by weight), and the A280 of each pool is determined.

The final purification step involves the use of a size-exclusion HPLC column. A Toso Hass TSK-GEL G2000-SWXL, 30 cm×7.8 mm ID column is equilibrated with 0.2M Tris-SO$_4$, 0.2M Na$_2$SO$_4$, at 1 mL/min. No more than 400 μl of DEAE HPLC Peak 1 pool is loaded on the column, and the eluate is monitored at 280 nm. The large peak which elutes at about 10 minutes from injection is collected. The absorbance is allowed to rise significantly above baseline before starting the collection. The volume (by weight) is measured, and the A280 of the peak fraction is determined. EDTA (ethylene diamine (dinitrilo) tetraacetic acid) is added from a 0.25M, pH 8.0, stock to the peak fraction to get a final concentration of 1 mM, and dithiothreitol [DTT] (from a 100 mM stock) is added to a final concentration of 0.1 mM. The purified UNG can be stored at 4° C.

The product is evaluated using standard methods. The concentration of purified UNG samples is determined by the absorbance at 280 nm. The extinction coefficient of UNG, calculated from the amino acid composition (*Analytic. Biochem.* 182:319–323, 1989), is 1.6 A280, 0.1%, cm. The purity of the final product is determined by SDS-PAGE analysis on Pharmacia Phast gels (see above), with a silver staining method adapted to the Phast Gel system (Heukeshoven and Dernick, 1988, *Electrophoresis* 9:28–32). An alternate purification method is shown in Example 5.

Example 4

Overexpression of Taq DNA Polymerase in an UNG and a dUTPase Deficient Host

A nucleic acid-free Taq DNA polymerase is overexpressed in *E. coli* and purified essentially as described in EP No. 0258,017 and U.S. Ser. No. 143,441, filed on Jan. 12, 1988, now abandoned (both of which are incorporated herein by reference), with exception that the cell host is dut- and ung-.

Representative *E. coli* K12 dut- and UNG- strains are: BW313, BD896 (*Gene* 28:211–219, 1984), and CJ236/pCJ105 available from Bio-Rad Laboratories (Richmond, Cali.) as part of the Muta-gene in vitro Mutagenis Kit. *E. coli* K12 strain BW313 is transformed to ampicillin resistance with plasmid pLSG10 (as described in U.S. Ser. No. 143,441).

*E. coli* K12 BW313/pLSG10 is grown at 32° C. in the presence of low level tryptophan (see U.S. Patent No. 4,499,188). When the available tryptophan has become limiting, the culture is shifted to 37° C. Depletion of tryptophan from the media and the temperature dependent-increased copy number provided by pLSG10 result in derepression of the trp promoter (operator) and synthesis of Taq DNA polymerase.

Taq DNA polymerase is purified according to a modification of the procedure described in U.S. Ser. No. 143,441. The phenyl sepharose eluate pool is dialyzed into 25 mM Tris-HCl, pH 8.3, 50 mM KCl, and 2.0 mM EDTA and treated with uracil N-glycosylase ($10^2$–$10^3$ units/milligram of polymerase protein at 37° C., 15 minutes). The sample is then heated to 75° C. for 15 minutes, cooled to 4° C., adjusted to 0.1M KCl, and applied to a heparin sepharose column.

The column is washed with 50 mM Tris-HCl, pH 7.5; 0.1 mM EDTA, and 0.2% Tween 20 (buffer B) containing 0.15M KCl. The glycosylase-treated Taq DNA polymerase is eluted with a linear gradient of 0.15 to 0.65M KCl in buffer B. Taq DNA polymerase elutes as a single peak at about 0.29M KCl. The purified DNA-free Taq DNA polymerase is diafiltered into sterile 50 mM Tris-HCl, pH 8.0, 250 mM KCl, 0.25 mM EDTA, 0.5% Tween-20 (Pierce, Surfact-AMPS), and 2.5 mM dithiothreitol (2.5× storage buffer without glycerol). The dialyzed DNA-free Taq DNA polymerase is diluted with 1.5 volumes of sterile (autoclaved) 80% (w/v) glycerol and stored at −20° C.

The above expression/purification scheme is generally applicable to any protein, including other thermostable nucleic acid polymerases and may be so utilized with only routine modification.

Example 5

Purification of Uracil N-Glycosylase

A 10 L batch of induced *E. coli* DG116/pFC101 cells produces about 500 to 1,000 g of cell pellet. One gram of cell pellet yields about 9 mg of UNG, and 1 mg of UNG is about $2.2 \times 10^6$ units of UNG. Although one gram of cell pellet produces large amounts of UNG enzyme, the cells are somewhat resistant to lysis by sonication, which is the method of choice for lysing small amounts of cells.

However, the cells are much more efficiently lysed using a Microfluidizer. This instrument requires about 50 g of material, which in mm contains more UNG than needed even for long term commercial purposes. Not all of the cell lysate need be processed, however, and the purification can be stopped at various points, allowing for long-term storage of excess material.

Thus, about 50 g of cell pellet are placed into a heat-treated glass beaker, and 5 mL of UNG lysis buffer are added per gram of cell pellet. UNG lysis buffer is 0.05M Tris-HCl, pH 8.0, and 1.0 mM EDTA. DTT can be added (at 0.1 mM) but is not required. The cell pellet is resuspended with a blender or motorized stirrer on a low setting.

The cells are lysed by passing the mixture twice through the Microfluidizer at 10,000 psi, and the lysate is divided between an appropriate number of heat-treated 15 mL Corex Centrifuge tubes. The tubes are then centrifuged for 30 minutes at 10,000×g at 2° to 8° C. The supernatant is decanted, retained, and filtered through a 0.45 micron filter using a disposable syringe. Until familiar with the procedure, one should retain aliquots or samples from each step of the purification process to check that each step gives the desired result. Monitoring the presence or absence of the desired band on SDS-PAGE gels is an easy way to check the success of each step.

The crude UNG preparations is next passed through a DEAE Sepharose column. The column is prepared with a bed volume of approximately 6 mL of DEAE Sepharose Fast Flow (Pharmacia, #17-0709-09). The column is first washed at least 10 bed volumes of 50 mM Tris-HCl (Tris is hydroxymethyl aminomethane), 1 mM EDTA, 1.0M NaCl, pH 8.0, and then equilibrated with at least 10 bed volumes of 50 mM Tris-HCl, 1 mM EDTA, pH 8.0, at a flow rate of approximately 60 cm/hr. About 6 mL of the filtered cell supernatant are loaded onto the gel and eluted with 50 mM Tris-HCl, 1 mM EDTA, at pH 8.0, and fractions of approximately 0.5 mL are collected. The remainder of the filtered cell supernatant can be stored frozen. The fractions are analyzed for absorbance at 280 nm. When a peak of A280 elutes and absorbance begins to drop, indicating that undesired material has been washed from the column (about 3 column volumes), the elution buffer is changed to 50 mM Tris, 1 mM EDTA, 0.3M NACl, pH 8.0. The second A280 peak to elute is the UNG activity peak. To regenerate the column after the UNG activity peak is collected, the elution buffer is changed to 50 mM Tris-HCl, 1.0 mM EDTA, 1.0M NaCl, pH 8.0, and elution is continued (about 3 column volumes) until a third peak elutes, and the eluate absorbance returns to baseline.

The fractions of the second peak (the one which eluted with 0.3M NaCl) are pooled, the volume of the pool calculated by weight, assuming a density of 1.0, and the A280 of the pool measured. During the elution of the second peak (about 4 column volumes), fractions of 0.1 column volumes are collected. The pooled second peak fractions are dialyzed for four hours in at least 100 volumes of 20 mM Tris-HCl, 1 mM EDTA, pH 8.0. The dialysis tubing should have a molecular weight cut-off of 12,000 to 14,000, should be only about ⅔ full, and should be sealed with double knots or secure clips. After dialysis, the dialyzed material should be centrifuged or filtered through a 0.22 micron vacuum filtration unit to remove debris. The dialyzed pool may be stored at −15° C.

The semi-purified preparations are then subjected to anion-exchange HPLC. The following HPLC buffers are prepared: Buffer A=20 mM Tris-SO₄, pH 8.0, and Buffer B=20 mM Tris-SO₄, 0.5M Na₂SO₄, pH 8.0 (a spectral grade of Na₂SO₄, e.g., Fluka #71969, is used).

A Bio-Gel DEAE-5-PW HPLC column (Bio-Rad Laboratories) is washed with at least 3 to 10, typically 5, bed volumes of Buffer B and then equilibrated with at least 5 bed volumes of 5% Buffer B/95% Buffer A, at a flow rate of 1.0 mL/min. The pumps and lines are primed and washed with Buffer A or Buffer B, as appropriate.

About 5 O.D. units at A280, typically about 1.0 mL, of the dialyzed DEAE sepharose pool are loaded onto the column and elution continued with the 5% Buffer B/95% Buffer A mixture for 5 minutes, then a 5 to 13% gradient of Buffer B (to Buffer A) is run over 15 minutes. Then, a 13 to 100% gradient of Buffer B is run over five minutes. Then, 100% Buffer B is run for 5 minutes, followed by a 100% to 5% gradient of Buffer B over 5 minutes, followed by a five minute run of 5% Buffer B for 5 minutes, at which time the column is ready for re-use.

The eluate is monitored at 280 nm. Two large UNG-containing peaks should elute at between 15 and 25 minutes (total elapsed time from injection). The peaks are collected separately. The fast peak, eluting at lower salt concentration is Peak 1. The fractions may be stored at 4° C. The anion-exchange HPLC is repeated as many times as necessary to obtain the amount of UNG desired. The Peak 1 and Peak 2 fractions are separately pooled, and the volume of the pools is measured (by weight), and the A280 of each pool is determined.

The two UNG peaks from anion exchange chromatography both have UNG activity and can both be used for purposes of the present invention. The second peak comprises a more negatively charged enzyme, presumably through derivatization of the lysine residue at position 15. in this purification procedure, however, one can resolve the two peaks. For the hydrophobic interaction chromatography (HIC) step described below, only the first peak from the anion exchange chromatography was used.

For each mL of Peak 1 pool, 0.5 mL of HIC Sample Buffer (0.3M sodium phosphate, pH 6, and 3M ammonium sulfate) is added and mixed. The volume of the resulting solution is calculated, and 0.18 mL of HIC Buffer B (0.1M sodium phosphate, pH 6, and 30% v/v propylene glycol) is added per mL of solution. Each HIC HPLC run should be with about the volume of solution that contains 1.50.D. (A280) units from the Peak 1 pool collected after the anion exchange chromatography step.

The HIC HPLC step is carried out on a Bio-Gel Phenyl-5-PW column (Bio-Rad). The HPLC pumps and lines are primed and washed with HIC Buffer B or HIC Buffer A (0.1M sodium phosphate, pH 6, and 1M ammonium sulfate), as appropriate. The HPLC is equilibrated (with at least 5 column volumes at a flow rate of 1.0 mL/minute) with 15% Buffer B (to 85% Buffer A) and programmed as shown below.

| Time | Action |
| --- | --- |
| 0.00 | Flow = 1.0 mL/min, % B = 15.00 |
| 1.00 | Injection, start integration (optional) |
| 5.00 | Flow = 1.0 mL/min, % B = 15.00 |
| 18.00 | Flow = 1.0 mL/min, % B = 40.00 |
| 23.00 | Flow = 1.0 mL/min, % B = 100.00 |
| 30.00 | Flow = 1.0 mL/min, % B = 100.00 |
| 35.00 | Flow = 1.0 mL/min, % B = 15.00 |
| 50.00 | Flow = 1.0 mL/min, % B = 15.00 |

The first major UNG-containing peak elutes 10 to 18 minutes after injection. The effluent is collected in sterile 12×75 mm propylene tubes when the O.D. 280 (A280) of the first major peak rises about 0.2 AU above the baseline. Collection is stopped when the peak stops falling and begins to deflect upwards again. For storage, about 4 mL of Storage Buffer (30 mM Tris-HCl, pH 7.5; 150 mM NaCl; 1 mM EDTA; 1 mM DTT; 5% v/v glycerol; and 0.05% Tween 20) are added per mL of effluent collected.

The above procedure produces very pure UNG, over 99% pure as determined by silver-stained gel analysis, more pure than prior art preparations. In addition, no single-stranded or double-stranded endonuclease activities were detected when 5 units of UNG were incubated at 37° C. for 1 hour with 1.2 μg of circular M13 DNA or 600 ng of supercoiled pBR322 (dcm-,dam-) in a final volume of 50 μL, respectively; no double-stranded exonuclease activity was detected when 5 units of UNG were incubated at 37° C. for 30 minutes with 1 pmole of [$^3$H]-dT-labeled 500 bp lambda PCR product in a final volume of 50 μgL; no 5'-single-stranded exonuclease activity was detected when 5 units of UNG were incubated at 37° C. for 30 minutes with 0.3 pmoles of a 5'-[$^{32}$P]-labeled oligonucleotide (41mer) in a final volume of 50 μgL; and no 3'-single-stranded exonuclease activity was detected when 5 units of UNG were incubated at 37° C. for 30 minutes with an oligonucleotide (40mer) labeled at the 3' end with α[$^{32}$P]-cordycepin in a final volume of 50 μ.

EXAMPLE 6

Reduction of Non-Specific Amplification

Non-specific amplifications originate from non-specific annealing of primers during PCR set-up and subsequent extension. With the incorporation of both dUTP and UNG, carryover dU-products and dU-extensions that occur prior to UNG inactivation (above 60° C.) are cleaved by the enzyme.

In dUTPNG amplifications, a 0 to 10 minute preincubation with UNG at 25° to 37° C. is recommended to remove carryover contaminants. However, UNG has greatest activity between 40° and 50° C., and the incorporation of a short preincubation step with UNG at these temperatures provides the best reduction of non-specific amplification. Because Taq polymerase has relatively minimal activity at these temperatures, UNG restriction is not compromised by overwhelming Taq extensions.

HIV or HTLV plasmid DNA was spiked into a clinical negative lysate and treated either with or without 2 units of UNG and with or without preincubation at either 37°, 45°, 50°, 55°, 60°, or 65° C. for 1 to 5 minutes. HIV samples were amplified with SK462–431; HTLV-I with SK432–111. All samples were typically amplified for 40 cycles with the following parameters: 1'95° C., 30"55° C., and 1'72° C. To prevent reactivation of UNG, reactions were either held overnight at 72° C. before extraction with chloroform or were immediately extracted with chloroform and analyzed by gel electrophoresis.

The amount of non-specific amplification is primer pair dependent. Because the HTLV primers SK432–111 are less specific than the HIV primers SK462–431, the effect of UNG is more dramatic. In the absence of UNG, with or without preincubation, substantial amounts of non-specific products were amplified in both systems. With the incorporation of UNG, non-specific amplifications were dramatically reduced. In the HTLV system, the incorporation of UNG alone reduces the non-specific bands observed after 30 cycles of amplification. However, after 40 cycles, the non-specific bands appear identical to the untreated samples, suggesting that UNG alone is insufficient in preventing these products from serving as targets.

By incorporating a preincubation step, these non-specific amplifications were further reduced. There is a broad temperature range at which the preincubation is helpful. Reactions which were "preincubated" at room temperature prior to cycling had much more background than those preincubated for 2 minutes at 37° to 60° C. While all preincubations in this temperature range worked, preincubations between 45° to 60° C. consistently gave less background. A 65° C. preincubation did not reduce background.

In the HTLV system, the extent of background reduction varied from experiment to experiment, but the true product band was invariably one of the major species formed in amplifications with UNG preincubation.

In the presence of UNG alone without preincubation, the major band was a non-specific product. As previously mentioned, the HIV primers are more specific, and the true product in the HIV amplification is the major band. After 40 cycles of amplification, substantial amounts of primer-dimers were formed in both systems.

An incubation of at least 2 minutes is recommended, as shorter times have led to more non-specific bands. No significant differences exist between 2 and 5 minutes of preincubation, and longer pretreatment times are unnecessary.

Incorporation of a 2 minute preincubation step into dUTP/UNG PCR procedure enables low copy amplifications of HIV-1 with SK462–431 that can be visualized by gel electrophoresis followed by ethidium bromide staining. With HTLV-I, 20 copies can be visualized by ethidium bromide, but below this level detection is compromised due to the presence of a non-specific band that co-migrates with the true product and by the presence of primer-dimers.

We claim:

1. A method for reducing non-specific amplification in a primer-based amplification reaction carried out in a reaction mixture, said method comprising:
   (a) incorporating into said reaction mixture a modified nucleoside triphosphate that is dUTP so that any newly synthesized nucleic acid contains a modified nucleotide; and further incorporating into said reaction mixture a glycosylase that is UNG that degrades nucleic acid containing said modified nucleotide;
   (b) incubating the reaction mixture of step (a) at a temperature between 45° C. and 60° C. for a time sufficient to degrade newly synthesized nucleic acid containing said modified nucleotide; and
   (c) carrying out said amplification reaction at or above 55° C.

2. The method of claim 1, wherein the amplification reaction is a polymerase chain reaction and the reaction mixture contains a thermostable DNA polymerase.

3. The method of claim 2, wherein the incubation step of (b) is carried out for 2 to 5 minutes.

4. The method of claim 3, wherein the thermostable polymerase is Taq polymerase.

* * * * *

UNITED STATES PATENT AND TRADEMARK OFFICE
CERTIFICATE OF CORRECTION

PATENT NO. : 5,418,149  
DATED : May 23, 1995  
INVENTOR(S) : Shirley Y. Kwok

Page 1 of 4

It is certified that error appears in the above-identified patent and that said Letters Patent is hereby corrected as shown below:

On title page, and col. 1, lines 1-4, in title, after "AMPLIFICATION" delete "GLYCOSYLASE USING DUTP AND DNA URACIL" and insert therefor --USING DUTP AND URACIL DNA GLYCOSYLASE--.

On the coversheet, in the section entitled "Inventors" please delete "David H. Gelfand, Oakland;".

On the coversheet, in the section entitled "Inventors" after "San Ramon" please delete "; John J. Sninsky, El Sobrante, all of".

In the Abstract, line 6, after "nucleotide" please delete "bags" and insert therefor --bases--.

Column 1, line 58, please delete "generic" and insert therefor --genetic--.

Column 2, line 57, please delete "hat" and insert therefor --heat--.

Column 3, line 31, please delete "LING" and insert therefor --UNG--.

Column 7, line 44, please delete "an" and insert therefor --art--.

Column 9, line 6, please delete "an" and insert therefor --art--.

Column 9, line 17, please delete "dTTp" and insert therefor --dTTP--.

Column 11, line 17, please delete "Oβ" and insert therefor --Qβ--.

Column 11, line 61, please delete "ill vitro" and insert therefor --*in vitro*--.

Column 12, line 6, please delete "CDNA" and insert therefor --cDNA--.

Column 12, line 16, please delete "convened" and insert therefor --converted--.

Column 12, line 39, please delete "mariner" and insert therefor --manner--.

Column 13, line 22, please delete "dTYP" and insert therefor --dTTP--.

Column 13, line 26, please delete "dTYP" and insert therefor --dTTP--.

UNITED STATES PATENT AND TRADEMARK OFFICE
CERTIFICATE OF CORRECTION

PATENT NO. : 5,418,149                 Page 2 of 4

DATED : May 23, 1995

INVENTOR(S) : Shirley Y. Kwok

It is certified that error appears in the above-identified patent and that said Letters Patent is hereby corrected as shown below:

Column 13, line 29, please delete "MgCI₂" and insert therefor --MgCl$_2$--.

Column 13, line 38, please delete "Used" and insert therefor --used--.

Column 13, line 43, please delete "eases" and insert therefor --cases--.

Column 14, line 55, please delete "Art" and insert therefor --An--.

Column 16, line 50, please delete "Urcil" and insert therefor --Uracil--.

Column 17, line 25, please delete "LING" and insert therefor --UNG--.

Column 18, line 31, please delete "Post-PCR" and insert therefor --post-PCR--.

Column 21, bridging lines 52 and 53, please delete "be-mused" and insert therefor --be used--.

Column 23, line 46, please delete "MgCI₂" and insert therefor --MgCl$_2$--.

Column 23, line 62, please delete "if" and insert therefor --If--.

Column 25, line 47, please delete "an" and insert therefor --art--.

Column 25, line 55, please delete "pan" and insert therefor --part--.

Column 25, line 61, please delete "Where" and insert therefor --where--.

Column 26, line 22, please delete "an" and insert therefor --art--.

Column 26, line 28, please delete "mcil" and insert therefor --uracil--.

Column 27, line 47, please delete "an" and insert therefor --art--.

Column 28, line 8, please delete "arc" and insert therefor --are--.

Column 28, line 31, please delete "Tan" and insert therefor --_Taq_--.

Column 28, line 51, please delete "UNO" and insert therefor --UNG--.

Column 29, line 10, please delete "SKI 111" and insert therefor --SK111--.

UNITED STATES PATENT AND TRADEMARK OFFICE
CERTIFICATE OF CORRECTION

PATENT NO. : 5,418,149
DATED : May 23, 1995
INVENTOR(S) : Shirley Y. Kwok

It is certified that error appears in the above-identified patent and that said Letters Patent is hereby corrected as shown below:

Column 29, line 40, please delete "5'-GTGGTGGATTG-" and insert therefor --5'GTGGTGGATTTG- --.

Column 29, line 54, please delete "CAGCCATGCCATGCAAT" and insert therefor --CAGCCATGCAAT--.

Column 29, line 62, please delete "GACAAATGGGGAT" and insert therefor --GCAGAATGGGAT--.

Column 30, line 48, please delete "bglII" and insert therefor --BglII--.

Column 31, line 4, please delete "ampicillinresistant" and insert therefor --amplicillin-resistant--.

Column 33, line 66, please delete "mm" and insert therefor --turn--.

Column 35, line 33, please delete "in" and insert therefor --In--.

Column 36, line 19, please delete "µgL" and insert therefor --µL--.

Column 36, line 23, please delete "µgL" and insert threfor --µL--.

Column 36, line 27, please delete "µ" and insert therefor --µL--.

UNITED STATES PATENT AND TRADEMARK OFFICE
CERTIFICATE OF CORRECTION

PATENT NO. : 5,418,149
DATED : May 23, 1995
INVENTOR(S) : Shirley Y. Kwok

It is certified that error appears in the above-indentified patent and that said Letters Patent is hereby corrected as shown below:

Column 36, line 38, please delete "dUTPNG" and insert therefor --dUTP/UNG--.

Signed and Sealed this

Twenty-sixth Day of March, 1996

Attest:

BRUCE LEHMAN

Attesting Officer    Commissioner of Patents and Trademarks